(12) United States Patent
Weng et al.

(10) Patent No.: US 12,049,665 B2
(45) Date of Patent: Jul. 30, 2024

(54) METHODS AND COMPOSITIONS FOR FORMING LIGATION PRODUCTS

(71) Applicant: AccuraGen Holdings Limited, Grand Cayman (KY)

(72) Inventors: Li Weng, Fremont, CA (US); Malek Faham, Burlingame, CA (US)

(73) Assignee: ACCURAGEN HOLDINGS LIMITED, George Town (KY)

( * ) Notice: Subject to any disclaimer, the term of this patent is extended or adjusted under 35 U.S.C. 154(b) by 735 days.

(21) Appl. No.: 17/251,116

(22) PCT Filed: Jun. 11, 2019

(86) PCT No.: PCT/US2019/036608
§ 371 (c)(1),
(2) Date: Dec. 10, 2020

(87) PCT Pub. No.: WO2019/241290
PCT Pub. Date: Dec. 19, 2019

(65) Prior Publication Data
US 2021/0254134 A1    Aug. 19, 2021

Related U.S. Application Data

(60) Provisional application No. 62/684,057, filed on Jun. 12, 2018.

(51) Int. Cl.
*C12Q 1/6806* (2018.01)
*C12Q 1/6855* (2018.01)
(Continued)

(52) U.S. Cl.
CPC ......... *C12Q 1/6806* (2013.01); *C12Q 1/6855* (2013.01); *C12Q 1/6874* (2013.01); *C12Q 1/6876* (2013.01); *C12Q 1/34* (2013.01)

(58) Field of Classification Search
None
See application file for complete search history.

(56) References Cited

U.S. PATENT DOCUMENTS 5,130,238 A    7/1992   Malek et al.
5,234,809 A    8/1993   Boom et al.
(Continued)

FOREIGN PATENT DOCUMENTS

AU    9057901 A    3/2002
CN    101432439 A    5/2009
(Continued)

OTHER PUBLICATIONS

Van Nieuwerburgh et al PLoS One. Oct. 28, 2011. 6(10): e26969 and Supplementary Materials and Methods, 15 pages total (Year: 2011).*

(Continued)

*Primary Examiner* — Carla J Myers
(74) *Attorney, Agent, or Firm* — WILSON SONSINI GOODRICH & ROSATI

(57) ABSTRACT

In some aspects, the present disclosure provides methods for forming ligation products comprising single-stranded polynucleotides without the need for enriching the single-stranded polynucleotides. Ligation products formed by various aspects of the present disclosure can be useful for various applications, including but not limited to sequence analysis. In some embodiments, the ligation products comprise cell-free polynucleotides. In some aspects, the present disclosure provides reaction mixtures, kits and complexes consistent with the methods herein.

15 Claims, 4 Drawing Sheets

(51) Int. Cl.
*C12Q 1/6874* (2018.01)
*C12Q 1/6876* (2018.01)
*C12Q 1/34* (2006.01)

(56) References Cited

U.S. PATENT DOCUMENTS

| | | |
|---|---|---|
| 5,270,184 A | 12/1993 | Walker et al. |
| 5,310,652 A | 5/1994 | Gelfand et al. |
| 5,322,770 A | 6/1994 | Gelfand |
| 5,330,892 A | 7/1994 | Vogelstein et al. |
| 5,352,775 A | 10/1994 | Albertsen et al. |
| 5,362,623 A | 11/1994 | Vogelstein et al. |
| 5,399,491 A | 3/1995 | Kacian et al. |
| 5,455,166 A | 10/1995 | Walker |
| 5,480,784 A | 1/1996 | Kacian et al. |
| 5,492,808 A | 2/1996 | De La Chapelle et al. |
| 5,494,810 A | 2/1996 | Barany et al. |
| 5,527,670 A | 6/1996 | Stanley |
| 5,527,676 A | 6/1996 | Vogelstein et al. |
| 5,545,540 A | 8/1996 | Mian |
| 5,571,905 A | 11/1996 | Vogelstein et al. |
| 5,576,422 A | 11/1996 | Vogelstein et al. |
| 5,591,826 A | 1/1997 | De La Chapelle et al. |
| 5,648,212 A | 7/1997 | Albertsen et al. |
| 5,648,245 A | 7/1997 | Fire et al. |
| 5,691,454 A | 11/1997 | Albertsen et al. |
| 5,693,470 A | 12/1997 | De La Chapelle et al. |
| 5,693,536 A | 12/1997 | Vogelstein et al. |
| 5,705,365 A | 1/1998 | Ryder et al. |
| 5,705,628 A | 1/1998 | Hawkins |
| 5,710,029 A | 1/1998 | Ryder et al. |
| 5,783,666 A | 7/1998 | Albertsen et al. |
| 5,807,692 A | 9/1998 | Kinzler et al. |
| 5,830,676 A | 11/1998 | Vogelstein et al. |
| 5,830,711 A | 11/1998 | Barany et al. |
| 5,834,252 A | 11/1998 | Stemmer et al. |
| 5,837,443 A | 11/1998 | De La Chapelle et al. |
| 5,854,033 A | 12/1998 | Lizardi |
| 5,871,925 A | 2/1999 | De La Chapelle et al. |
| 5,871,968 A | 2/1999 | Kinzler et al. |
| 5,888,779 A | 3/1999 | Kacian et al. |
| 5,939,291 A | 8/1999 | Loewy et al. |
| 5,942,391 A | 8/1999 | Zhang et al. |
| 5,955,263 A | 9/1999 | Vogelstein et al. |
| 6,033,850 A | 3/2000 | Purvis |
| RE36,713 E | 5/2000 | Vogelstein et al. |
| 6,090,566 A | 7/2000 | Vogelstein et al. |
| 6,114,124 A | 9/2000 | Albertsen et al. |
| 6,143,495 A | 11/2000 | Lizardi et al. |
| 6,156,504 A | 12/2000 | Gocke et al. |
| 6,210,891 B1 | 4/2001 | Nyren et al. |
| 6,245,515 B1 | 6/2001 | Vogelstein et al. |
| 6,251,639 B1 | 6/2001 | Kurn |
| 6,277,605 B1 | 8/2001 | Wijnhoven et al. |
| 6,300,059 B1 | 10/2001 | Vogelstein et al. |
| 6,333,157 B1 | 12/2001 | Miller-Jones et al. |
| 6,380,369 B1 | 4/2002 | Adams et al. |
| 6,410,278 B1 | 6/2002 | Notomi et al. |
| 6,413,727 B1 | 7/2002 | Albertsen et al. |
| 6,416,984 B1 | 7/2002 | Haseltine et al. |
| 6,482,606 B1 | 11/2002 | Adams et al. |
| 6,511,805 B1 | 1/2003 | Gocke et al. |
| 6,521,409 B1 | 2/2003 | Gocke et al. |
| 6,569,647 B1 | 5/2003 | Zhang et al. |
| 6,582,908 B2 * | 6/2003 | Fodor ............... C12Q 3/00 506/30 |
| 6,593,086 B2 | 7/2003 | Zhang |
| 6,610,477 B1 | 8/2003 | Haseltine et al. |
| 6,620,619 B2 | 9/2003 | Haseltine et al. |
| 6,677,312 B1 | 1/2004 | Vogelstein et al. |
| 6,800,617 B1 | 10/2004 | Vogelstein et al. |
| 6,815,167 B2 | 11/2004 | Crothers et al. |
| 6,833,246 B2 | 12/2004 | Balasubramanian |
| 6,917,726 B2 | 7/2005 | Levene et al. |
| 6,939,675 B2 | 9/2005 | Gocke et al. |
| 6,946,251 B2 | 9/2005 | Kurn |
| RE38,916 E | 12/2005 | Vogelstein et al. |
| 6,977,148 B2 | 12/2005 | Dean et al. |
| 7,001,724 B1 | 2/2006 | Greenfield |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,087,583 B2 | 8/2006 | Vogelstein et al. |
| 7,170,050 B2 | 1/2007 | Turner et al. |
| 7,183,053 B2 | 2/2007 | Gocke et al. |
| 7,208,275 B2 | 4/2007 | Gocke et al. |
| 7,267,955 B2 | 9/2007 | Vogelstein et al. |
| 7,282,335 B2 | 10/2007 | Gocke et al. |
| 7,288,380 B1 | 10/2007 | Gocke et al. |
| 7,326,778 B1 | 2/2008 | De La Chapelle et al. |
| 7,361,466 B2 | 4/2008 | Korlach et al. |
| 7,387,874 B2 | 6/2008 | Gocke et al. |
| 7,399,592 B2 | 7/2008 | Gocke et al. |
| 7,410,764 B2 | 8/2008 | Gocke et al. |
| 7,416,844 B2 | 8/2008 | Korlach et al. |
| 7,424,368 B2 | 9/2008 | Huang et al. |
| 7,537,897 B2 | 5/2009 | Brenner et al. |
| 7,553,619 B2 | 6/2009 | Kumar et al. |
| 7,569,349 B2 | 8/2009 | Gocke et al. |
| 7,569,350 B2 | 8/2009 | Gocke et al. |
| RE40,948 E | 10/2009 | Vogelstein et al. |
| 7,700,286 B2 | 4/2010 | Stroun et al. |
| RE41,327 E | 5/2010 | Gocke et al. |
| 7,790,395 B2 | 9/2010 | Gocke et al. |
| 7,824,890 B2 | 11/2010 | Hoser et al. |
| 7,935,484 B2 | 5/2011 | Gocke et al. |
| 7,935,487 B2 | 5/2011 | Gocke et al. |
| 7,972,817 B2 | 7/2011 | Kopreski |
| 8,048,629 B2 | 11/2011 | Gocke et al. |
| 8,209,130 B1 | 6/2012 | Kennedy et al. |
| 8,361,726 B2 | 1/2013 | Gocke et al. |
| 8,563,477 B2 | 10/2013 | Smith et al. |
| RE44,596 E | 11/2013 | Stroun et al. |
| 8,835,358 B2 | 9/2014 | Fodor et al. |
| 8,916,351 B2 | 12/2014 | Murakami |
| 9,217,167 B2 | 12/2015 | Heller et al. |
| 9,260,753 B2 | 2/2016 | Xie et al. |
| 9,586,987 B2 | 3/2017 | Hayashizaki et al. |
| 10,155,980 B2 | 12/2018 | Weng et al. |
| 10,227,584 B2 | 3/2019 | Emerick et al. |
| 10,443,087 B2 | 10/2019 | Rigatti et al. |
| 10,724,088 B2 | 7/2020 | Weng et al. |
| 10,752,942 B2 | 8/2020 | Weng et al. |
| 10,767,222 B2 | 9/2020 | Lin et al. |
| 11,286,519 B2 | 3/2022 | Weng et al. |
| 11,427,866 B2 | 8/2022 | Faham et al. |
| 11,578,359 B2 | 2/2023 | Weng et al. |
| 11,597,973 B2 | 3/2023 | Tang |
| 11,643,683 B2 | 5/2023 | Weng et al. |
| 2002/0042061 A1 | 4/2002 | Yang et al. |
| 2002/0168645 A1 | 11/2002 | Taylor |
| 2003/0032024 A1 | 2/2003 | Lizardi |
| 2003/0100077 A1 | 5/2003 | Korte et al. |
| 2003/0207295 A1 | 11/2003 | Gunderson et al. |
| 2004/0058378 A1 | 3/2004 | Kong et al. |
| 2004/0067511 A1 | 4/2004 | Thomas |
| 2006/0029953 A1 | 2/2006 | Sharf |
| 2006/0228721 A1 | 10/2006 | Leamon et al. |
| 2007/0020646 A1 | 1/2007 | Hoon et al. |
| 2007/0087362 A1 | 4/2007 | Church et al. |
| 2007/0099208 A1 | 5/2007 | Drmanac et al. |
| 2007/0134128 A1 | 6/2007 | Korlach |
| 2008/0021205 A1 | 1/2008 | Blau et al. |
| 2008/0039417 A1 | 2/2008 | Wang et al. |
| 2008/0160511 A1 | 7/2008 | Dawson et al. |
| 2009/0099041 A1 | 4/2009 | Church et al. |
| 2009/0136924 A1 | 5/2009 | Larionov et al. |
| 2010/0028873 A1 | 2/2010 | Belouchi et al. |
| 2010/0075384 A1 | 3/2010 | Kong et al. |
| 2010/0115744 A1 | 5/2010 | Fong |
| 2010/0291548 A1 | 11/2010 | Sharaf et al. |
| 2010/0304989 A1 | 12/2010 | Von Hoff et al. |
| 2011/0003705 A1 | 1/2011 | Lowe et al. |
| 2011/0151438 A9 | 6/2011 | Nautiyal et al. |

(56) References Cited

U.S. PATENT DOCUMENTS

| | | |
|---|---|---|
| 2011/0237444 A1 | 9/2011 | Clancy et al. |
| 2011/0288284 A1 | 11/2011 | Makarov |
| 2011/0319299 A1 | 12/2011 | Osborne et al. |
| 2012/0115744 A1 | 5/2012 | Raymond |
| 2012/0157326 A1 | 6/2012 | Tisi et al. |
| 2012/0164651 A1 | 6/2012 | Kazakov et al. |
| 2013/0116130 A1 | 5/2013 | Fu et al. |
| 2013/0178369 A1 | 7/2013 | Burns et al. |
| 2013/0217023 A1 | 8/2013 | Godwin et al. |
| 2013/0224740 A1 | 8/2013 | Thierry et al. |
| 2013/0244885 A1 | 9/2013 | Wang et al. |
| 2013/0331288 A1 | 12/2013 | Gunderson et al. |
| 2014/0051154 A1 | 2/2014 | Hyland et al. |
| 2014/0066317 A1 | 3/2014 | Talasaz |
| 2014/0121116 A1 | 5/2014 | Richards et al. |
| 2014/0154683 A1 | 6/2014 | Vogelstein et al. |
| 2014/0221329 A1 | 8/2014 | Cronin et al. |
| 2014/0227705 A1 | 8/2014 | Vogelstein et al. |
| 2014/0234850 A1 | 8/2014 | Zhang et al. |
| 2014/0274740 A1 | 9/2014 | Srinivasan et al. |
| 2014/0295498 A1 | 10/2014 | Turner et al. |
| 2014/0296081 A1 | 10/2014 | Diehn et al. |
| 2014/0336236 A1 | 11/2014 | Cronin et al. |
| 2015/0031035 A1 | 1/2015 | Kvam et al. |
| 2015/0033372 A1 | 1/2015 | Bradley et al. |
| 2015/0044687 A1 | 2/2015 | Schmitt et al. |
| 2015/0111789 A1 | 4/2015 | Betts et al. |
| 2015/0126376 A1 | 5/2015 | Bielas et al. |
| 2015/0133391 A1 | 5/2015 | De Vlaminick et al. |
| 2015/0141292 A1 | 5/2015 | Fodor et al. |
| 2015/0147815 A1 | 5/2015 | Babiarz et al. |
| 2015/0315636 A1 | 11/2015 | Nadeau et al. |
| 2015/0361492 A1 | 12/2015 | Vogelstein et al. |
| 2015/0366866 A1 | 12/2015 | Ali et al. |
| 2016/0040229 A1 | 2/2016 | Talasaz et al. |
| 2016/0145691 A1 | 5/2016 | Cronin et al. |
| 2016/0201135 A1 | 7/2016 | Cronin et al. |
| 2016/0319345 A1 | 11/2016 | Gnerre et al. |
| 2017/0204456 A1 | 7/2017 | Nobile et al. |
| 2017/0204459 A1 | 7/2017 | Barany et al. |
| 2017/0275609 A1 | 9/2017 | Geng et al. |
| 2017/0362639 A1 | 12/2017 | Wilson |
| 2018/0363039 A1 | 12/2018 | Weng et al. |
| 2018/0363052 A1 | 12/2018 | Schmitt et al. |
| 2019/0241935 A1 | 8/2019 | Makarov et al. |
| 2019/0323073 A1 | 10/2019 | Lin et al. |
| 2020/0080141 A1 | 3/2020 | Weng et al. |
| 2023/0287485 A1 | 9/2023 | Weng et al. |

FOREIGN PATENT DOCUMENTS

| | | |
|---|---|---|
| CN | 101935697 A | 1/2011 |
| CN | 101985654 A | 3/2011 |
| CN | 102625850 A | 8/2012 |
| CN | 103717752 A | 4/2014 |
| CN | 104745679 A | 7/2015 |
| CN | 104946737 A | 9/2015 |
| EP | 0684315 A1 | 11/1995 |
| EP | 0518650 B1 | 1/1997 |
| EP | 0390323 B1 | 12/1998 |
| EP | 0929694 A1 | 7/1999 |
| EP | 0580596 B1 | 7/2000 |
| EP | 0569527 B1 | 3/2001 |
| EP | 0730648 B1 | 8/2004 |
| EP | 2396430 B1 | 5/2013 |
| EP | 2722401 A1 | 4/2014 |
| EP | 2828218 A1 | 1/2015 |
| EP | 3080298 B1 | 10/2018 |
| JP | 2002503948 A | 2/2002 |
| JP | 2002538840 A | 11/2002 |
| JP | 2004512134 A | 4/2004 |
| JP | 2006516410 A | 7/2006 |
| JP | 2008526228 A | 7/2008 |
| JP | 2009500004 A | 1/2009 |
| JP | 2011505161 A | 2/2011 |
| JP | 2013143966 A | 7/2013 |
| JP | 2014138597 A | 7/2014 |
| JP | 2016507246 A | 3/2016 |
| WO | WO-9844151 A1 | 10/1998 |
| WO | WO-0004192 A1 | 1/2000 |
| WO | WO-0049176 A1 | 8/2000 |
| WO | WO-0055369 A1 | 9/2000 |
| WO | WO-0061741 A1 | 10/2000 |
| WO | WO-0118230 A1 | 3/2001 |
| WO | WO-0120035 A2 | 3/2001 |
| WO | WO-0138580 A2 | 5/2001 |
| WO | WO-2007024653 A2 | 3/2007 |
| WO | WO-2005026329 A3 | 8/2007 |
| WO | WO-2007133703 A2 | 11/2007 |
| WO | WO-2007140417 A2 | 12/2007 |
| WO | WO-2007140417 A3 | 2/2008 |
| WO | WO-2007024653 A3 | 4/2008 |
| WO | WO-2008070352 A3 | 10/2008 |
| WO | WO-2007117832 A3 | 12/2008 |
| WO | WO-2013074632 A1 | 5/2013 |
| WO | WO-2013142389 A1 | 9/2013 |
| WO | WO-2013181170 A1 | 12/2013 |
| WO | WO-2013181276 A1 | 12/2013 |
| WO | WO-2014014498 A1 | 1/2014 |
| WO | WO-2014015084 A2 | 1/2014 |
| WO | WO-2014070946 A1 | 5/2014 |
| WO | WO-2014145128 A2 | 9/2014 |
| WO | WO-2014176575 A1 | 10/2014 |
| WO | WO-2015079042 A1 | 6/2015 |
| WO | WO-2015089333 A1 | 6/2015 |
| WO | WO-2015100427 A1 | 7/2015 |
| WO | WO-2016053638 A1 | 4/2016 |
| WO | WO-2016187583 A1 | 11/2016 |
| WO | WO-2017062863 A1 | 4/2017 |
| WO | WO-2017096322 A1 | 6/2017 |
| WO | WO-2017201102 A1 | 11/2017 |
| WO | WO-2017223366 A1 | 12/2017 |
| WO | WO-2018035170 A1 | 2/2018 |
| WO | WO-2019241290 A1 | 12/2019 |
| WO | WO-2020049176 A1 | 3/2020 |

OTHER PUBLICATIONS

Gansuage et al Nucleic Acids Research. Jan. 24, 2017. 45(10): e79, 10 pages (Year: 2017).*

Delcher, et al. Alignment of whole genomes. Nucleic Acids Research. Feb. 2, 1999; 27(11): 2369-2376.

European Patent Application No. 16871682.7 Extended European Search Report dated Jul. 26, 2019.

Kent, W.J. Blat—The Blast-like alignment tool. Genome Research. 2002: 656-664.

Kurtz, et al. Versatile and open software for comparing large genomes. Genome Biol. 2004;5(2):R12. doi: 10.1186/GB-2004-5-2-r12. Epub Jan. 30, 2004.

Langmead et al. Ultrafast and memory-efficient alignment of short DNA sequences to the human genome. Genome biology 10:R25 (10 pgs) (2009).

Larkin, et al. Clustal W and Clustal X version 2.0. Bioinformatics applications note. 2007. 2947-2948; 23(21).

Li et al. Fast and accurate short read alignment with Burrows-Wheeler ransform. Bioinformatics 25:1754-60 (2009).

Lipman, et al. Rapid and sensitive protein similarity searches. Science. Mar. 22, 1985; 227(4693):1435-41.

PCT/US2016/064853 International Search Report and Written Opinion dated Feb. 7, 2017.

PCT/US2019/036608 International Search Report and Written Opinion dated Sep. 23, 2019.

Pearson et al. Improved Tools for Biological Sequence Comparison. PNAS USA 85:2444-48 (1988).

Sievers, et al. Fast, Scalable generation of high-quality protein multiple sequence alignments using clustal omega. Molecular systems biology. 2011.

Slater, et al. Automated generation of heuristics for biological sequence comparison. BMC Bioinformatics. Feb. 15, 2005; 6(31): 1-11.

(56) References Cited

OTHER PUBLICATIONS

Ali et al., Rolling circle amplification: a versatile tool for chemical biology, materials science and medicine. Chem Soc Rev 43(10): 3324-3341 (2014).
Amado, et al. Wild-type KRAS is required for panitumumab efficacy in patients with metastic colorectal cancer. Journal of Clinical Oncology. Apr. 1, 2008; 26(10);1626-1634.
Awuah, et al. Thermal inactivation kinetics of trypsin at aseptic processing temperatures. Journal of food process engineering 1993 v.16 No. 4 pp. 315-328 (abstract).
Beck, et al. Next generation sequencing of serum circulating nucleic acids from patients with invasive ductal breast cancer reveals differences to healthy and nonmalignant controls. Mol Cancer Res. Mar. 2010;8(3):335-42. doi: 10.1158/1541-7786.MCR-09-0314. Epub Mar. 9, 2010.
Bevan, et al., Sequencing of PCR-amplified DNA, PCR methods and applications, 1992; vol. 1: 222-228.
Blast. Basic local alignment search tool. Available at http://blast.ncbi.nlm.nih.gov/Blast.cgi. Accessed on Oct. 10, 2016.
Bokemeyer, et al. Fluorouracil, leucovorin, and oxaliplatin with and without cetuximab in the first-line treatment of metastatic colorectal cancer. Journal of Clinical Oncology. Feb. 10, 2009; 27(5).: 663-671.
Brenner. A cultivated taste for yeast. Genome Biol. 2000;1(1):Reviews103. Epub Apr. 27, 2000.
Brenner, C. Chemical genomics in yeast. Genome Biology. 2004; 5:240.
Brietbach et al. Direct Quantification of Cell-Free, Circulating DNA from Unpurified Plasma. PLoS One 9(3):1-11 (2014).
Creating Standard Curves with Genomic DNA or Plasmid DNA Templates for Use in Quantitative PCR. Applied Biosystems 2003. Downloaded Oct. 17, 2017. URL: http://www6.appliedbiosystems.com/support/tutorials/pdf/quant_pcr.pdf.
Dawson, et al., Analysis of circulating tumor DNA to monitor metastatic breast cancer. The New England Journal of Medicine. Mar. 28, 2013. 368(13); 1199-1209.
Dean et al., Comprehensive human genome amplification using multiple displacement amplification. Proc Natl Acad Sci USA 99(8): 5261-5266 (2002).
Dean, et al. Rapid amplification of plasmid and phage DNA using phi29 DNA polymerase and multiply-primed rolling circle amplification. Genome Research 11.6 (2001): 1095-1099.
Devonshire, Alison S et al. Towards standardisation of cell-free DNA measurement in plasma: controls for extraction efficiency, fragment size bias and quantification, Analytical and Bioanalytical Chemistry, 406(26): 6499-6512 (2014).
Dicker, et al. The detection of TP53 mutations in chronic lymphocytic leukemia independently predicts rapid disease progression and is highly correlated with a complex aberrant karyotype. Leukemia. Jan. 2009; 23(1):117-124.
Dillon L.W. et al. Production of Extrachromosomal MicroDNAs Is Linked to Mismatch Repair Pathways and Transcriptional Activity. Cell Rep. Jun. 23, 2015;11(11):1749-59.
Eason, et al. Characterization of synthetic DNA bar codes in *Saccharomyces cerevisiae* gene-deletion strains. Proc Natl Acad Sci U S A. Jul. 27, 2004; 101(30): 11046-11051.
Emboss. Emboss Needle: Pairwise Sequence Alignment (Nucleotide). Available at http://www.ebi.ac.uk/Tools/psa/emboss_needle/nucleotide.html. Accessed on Oct. 10, 2016.
Emboss. Emboss Water: Pairwise Sequence Alignment (Nucleotide). Available at http://www.ebi.ac.uk/Tools/psa/emboss_water/nucleotide.html. Accessed on Oct. 10, 2016.
Enari et al. A caspase-activated DNase that degrades DNA during apoptosis, and its inhibitor ICAD. Nature 391:43-50 (1998).
EP17816242 Extended European Search Report dated Nov. 25, 2019.
"Exonucleases" from Wikipedia. Printed on Sep. 14, 2023.
Faham M. et al. Deep-sequencing approach for minimal residual disease detection in acute lymphoblastic leukemia. Blood. Dec. 20, 2012;120(26):5173-80.

"Flap endonucleases" from Wikipedia. Printed on Sep. 14, 2023.
Florsheim, et al. Integrated Innate Mechanisms Involved in Airway Allergic Inflammation to the Serine Protease Subtilisin. J Immunol. May 15, 2015; 194(10): 4621-4630.
Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).
Freshney, Culture of animal cells: A manual of basic technique and specialized applications (6th Edition). John Wiley & Sons, Inc. (2010).
Giacona, et al. Cell-free DNA in human blood plasma: length measurements in patients with pancreatic cancer and healthy controls. Pancreas. Jul. 1998;17(1):89-97.
Giaever, et al. Chemogenomic profiling: identifying the functional interactions of small molecules in yeast. Proc Natl Acad Sci U S A. Jan. 20, 2004;101(3):793-8. Epub Jan. 12, 2004.
Guatelli et al. Isothermal, in vitro amplification of nucleic acids by a multienzyme reaction modeled after retroviral replication. PNAS USA 87(5):1874-1878 (1990).
Harkins, et al., Replicating fetal trisomy patient-like reference material for use in non-invasive prenatal screening tests. Sera Care. AMP 2015. Nov. 5-7, 2015.
Harlow, et al. Antibodies: A Laboratory manual. Cold Spring Harbor Laboratory. 1988.
Heinrich et al. Kinase mutations and imatinib response in patients with metastatic gastrointestinal stromal tumor. Journal of Clinical Oncology.Dec. 1, 2003; 21(23): 4342-4349.
Hindson, et al. High-throughput droplet digital PCR system for absolute quantitation of DNA copy number. Analytical Chemistry. 83(22):8604-8610 (2011).
Horizon Product Specification. cfDNA Reference Standard Set. 6068PSS-01(V-01). 2015.
Huang, S.H. Inverse polymerase chain reaction. An efficient approach to cloning cDNA ends. Mol Biotechnol. Aug. 1994;2(1):15-22.
Hussmann, et al. Reply to Schmitt et al.: Data-filtering schemes for avoiding double-counting in circle sequencing. PNAS. Apr. 22, 2014; 111(16).
Illumina. Genome Analyzer System. Available at http://support.illumina.com/content/dam/illumina-marketing/documents/products/datasheets/datasheet_genome_analyzeriix.pdf. Accessed onOct. 10, 2016.
Jahr, et al. DNA fragments in the blood plasma of cancer patients: quantitations and evidence for their origin from apoptotic and necrotic cells. Cancer Res. Feb. 15, 2001;61(4):1659-65.
Jeffreys et al. DNA Enrichment by Allele-Specific Hybridization (DEASH): A Novel Method for Haplotyping and for Detecting Low-Frequency Base Substitutional Variants and Recombinant DNA Molecules. Genome Research 13:2316-2324 (2003).
Jensen TJ et al., Noninvasive detection of a balanced fetal translocation from maternal plasma. Clin Chem. Oct. 2014;60(10):1298-305. Epub Jul. 16, 2014.
Jiang et al. The Long and Short of Circulating Cell-Free DNA and the Ins and Outs of Molecular Diagnostics. Trends Genet 32(6):360-371 (2016).
Katayama, et al. Mechanisms of acquired crizotinib resistance in ALK-rearranged lung cancers. Sci. Transl Med. Feb. 8, 2012; 8(4).
Konry T, Hayman RB, Walt DR. Microsphere-based rolling circle amplification microarray for the detection of DNA and proteins in a single assay. Anal Chem. Jul. 15, 2009;81(14):5777-82.
Kroenlein H. et al. Molecular analysis of the t(2;8)/MYC-IGK translocation in high-grade lymphoma/leukemia by long-distance inverse PCR. Genes Chromosomes Cancer. Mar. 2012;51(3):290-9.
Kumar, et al. Emerging technologies in yeast genomics. Nat Rev Genet. Apr. 2001;2(4):302-12.
Kumar et al. Normal and Cancerous Tissues Release Extrachromosomal Circular DNA (eccDNA) into the Circulation Mol Cancer Res 15(9):1197-1205 (2017).
Kurtz, et al. Versatile and open software for comparing large genomes. Biomed central. Jan. 30, 2004.
Landegren, U. Molecular mechanics of nucleic acid sequence amplification. Elsevier Science. Jun. 1993. 9(6). 199-204.

(56) References Cited

OTHER PUBLICATIONS

Lee, et al. Nucleic acid amplification technologies: application to disease diagnosis. Biotechniques books. 1997.
Li, et al. Fast and accurate long-read alignment with burrows-wheeler transform. Bioinformatics. Mar. 1, 2010;26(5):589-95.
Li et al., Fast and accurate short read alignment with Burrows-Wheeler transform. Bioinformatics. 25(14):1754-1760 (2009).
Li et al. Isothermally sensitive detection of serum circulating miRNAs for lung cancer diagnosis. Anal Chem. Dec. 3, 2013;85(23):11174-9.
Li, et al. Technical advance: Whole genome amplification of plasma-circulating DNA enables expanded screening for allelic imbalance in plasma. Journal of Molecular Diagnostics. Feb. 2006. 8(1); 22-30.
Lin, et al. Rolling Circle Enzymatic Replication of a Complex Multi-Crossover DNA Nanostructure. J Am Chem Soc. Nov. 21, 2007; 129(46): 14475-14481.
Liu W.H. et al. Inverse PCR-based RFLP scanning identifies low-level mutation signatures in colon cells and tumors. Cancer Res. Apr. 1, 2004;64(7):2544-51.
Lizardi, et al. Exponential amplification of recombinant-RNA hybridization probes. Biotechnology. 1988. 6:1197-1202.
Lou, et al. High-throughput DNA sequencing errors are reduced by orders of magnitude using circle sequencing. Proc Natl Acad Sci U S A. Dec. 3, 2013;110(49):19872-7. doi: 10.1073/pnas.1319590110. Epub Nov. 15, 2013.
Lou et al., Supporting Information for "High-throughput DNA sequencing errors are reduced by orders of magnitude using circle sequencing," Proc Natl Acad Sci U S A., 110(49):19872-7. doi: 10.1073/pnas.1319590110 (14 pages) (2013).
Lou et al. Bio Techniques, pp. 1-14 [Support Information to Lou et al. BioTechniques 110(49) publication] (2013).
Maldonado, et al. Determinants of BRAF mutations in primary melanomas. Journal of the National Cancer Institute. Dec. 17, 2003; 95(24):1878-1890.
Matta, et al. Isolation and partial characterization of a thermostable extracellular protease of Bacillus polymyxa B-17. Int J Food Microbiol. Jul. 21, 1998;42(3):139-45 (abstract).
McLendon, et al. Survival analysis of presumptive prognostic markers among oligodendrogliomas. John Wiley & Sons. Oct. 15, 2005; 104(8): 1693-1699.
McPherson, M. J. et al.(Eds.) PCR 2: A Practical Approach. Practical approach series. IRL Press. 1995. (Table of Contents).
Miller, et al. A simple salting out procedure for extracting DNA from human nucleated cells. Nucleic Acid Research. 1988; 16(3).
Misale, et al. Emergence of KRAS mutations and acquired resistance to anti-EGFR therapy in colorectal cancer. Nature. Jun. 13, 2012; 486(7404):532-536.
Mitchell, et al. Circulating MicroRNAs as Stable Blood-based Markers for Cancer Detection. Proceedings of the National Academy of Sciences of the United States of America. vol. 105, Issue. 30 (2008): pp. 10513-10518.
Mitsunobu et al.: Flap endonuclease activity of gene 6 exonuclease of bacteriophage T7. J Biol Chem. 289(9):5860-5875 doi:10.1074/jbc.M113.538611 (2014).
Moran et al., Heat-labile proteases in molecular biology applications. FEMS Microbiology Letters 197(1):59-63 (2001).
Nelson J.R. et al. TempliPhi, phi29 DNA polymerase based rolling circle amplification of templates for DNA sequencing. Biotechniques. Jun. 2002;Suppl:44-7. PMID: 12083397.
Neumann, et al., Frequency and type of KRAS mutations in routine diagnostic analysis of metastatic colorectal cancer. Pathol Res Pract. 2009;205(12):858-62.
Newman, et al. An ultrasensitive method for quantitating circulating tumor DNA with broad patient coverage. Nat Med. May 2014;20(5):548-54. Epub Apr. 6, 2014.
Novocraft Technologies SDN BHD. NovoAlign. Available at http://www.novocraft.com/products/novoalign/. Accessed on Oct. 10, 2016.
Ochman, et al. Genetic applications of an inverse polymerase chain reaction. Genetics. Nov. 1988;120(3):621-3.
Olivier, et al., TP53 mutations in human cancers: origins, consequences, and clinical use. Cold Spring Harb. Perspect Biology. 2010;1-17.
Pao, et al., EGF receptor gene mutations are common in lung cancers from "never smokers" and are associated with sensitivity of tumors to gefitinib and erlotinib. Proc. Natl. Acad. Sci. USA. Sep. 7, 2004; 101(36):13306-13311.
Paska et al. Effect of formalin, acetone, and RNAlater fixatives on tissue preservation and different size amplicons by real-time PCR from paraffin-embedded tissue. Diagn Mol Path 13(4): 234-240 (2004).
Pavlopoulos A. Identification of DNA sequences that flank a known region by inverse PCR. Methods Mol Biol. 2011;772:267-75.
Pinheiro et al., Evaluation of a Droplet Digital Polymerase Chain Reaction Format for DNA Copy Number Quantification. Analytical Chemistry. 84(2):1003-1011 (2012).
Polidoros, et al., Rolling circle amplification-RACE: A method for simultaneous isolation of 5' and 3' cDNA ends from amplified cDNA templates. BioTechniques 41.1 (Jul. 2006):35-42. including p. 1/1 of Supplementary Material.
Promega. Thermolysin—Thermostable Proteinase with High Digest Temperature; Better Denaturation, Digestion of Proteolytically Resistant Proteins. Available at https://www.promega.com/products/mass-spectrometry/proteases-and-surfactants/thermolysin/. Accessed Apr. 11, 2018.
Qiagen. How can Qiagen Protease and Proteinase K be inactivated? Available at https://www.qiagen.com/ca/resources/faq?id=d24681d7-88e7-421a-84d9-27bfd5141103&lang=en. Accessed Apr. 11, 2018.
Remacle, et al. Substrate Cleavage Analysis of Furin and Related Proprotein Convertases—A Comparative Study. J Biol Chem. Jul. 25, 2008; 283(30): 20897-20906.
Samuels, et al. High Frequency of Mutations of the PIK3CA Gene in Human Cancers. Science Mag. Apr. 23, 2004; 304.
Schmitt et al., Detection of ultra-rare mutations by next-generation sequencing. PNAS. 109(36):14508-14523 (2012).
Schmitt, et al. Risks of double-counting in deep sequencing. PNAS. Apr. 22, 2014;111(16).
Schubert J. et al. Surveying cereal-infecting geminiviruses in Germany—diagnostics and direct sequencing using rolling circle amplification. Virus Res. Jul. 2007;127(1):61-70.
SeraCare and NIST Partner on Development of Circulating Tumor DNA Reference Standards for Diagnostics (Press Release). SeraCare Life Sciences, Inc. Jul. 14, 2016 (2 pages).
Seraseq(TM) ctDNA: A Breakthrough QC Technology. SeraCare Life Sciences, Inc. (2017) 6 pages.
Shaw, et al. Clinical Features and Outcome of Patients With Non-Small-Cell Lung Cancer Who Harbor EML4-ALK. Journal of Clinical Oncology. Sep. 10, 2009; 27(26):4247-4253.
Shibata Y. et al. Extrachromosomal microDNAs and chromosomal microdeletions in normal tissues. Science. Apr. 6, 2012;336(6077):82-6. doi: 10.1126/science.1213307. Epub Mar. 8, 2012. Erratum in: Science. Jun. 22, 2012;336(6088):1506.
Sigma-Alorich. Protease from *Streptomyces griseus*. Available at https://www.sigmaaldrich.com/catalog/product/sigma/p6911?lang=en®ion=US#. Accessed Apr. 11, 2018.
Soap.Short Oligonucleotide Analysis Package. Available at http://soap.genomics.org.cn/. Accessed on Oct. 10, 2016.
Sourceforge-Maq-Mapping-and-Assembly-with-Qualities. Available at http://maq.sourceforge.net/. Accessed on Oct. 10, 2016.
Spargo, et al. Detection of M. tuberculosis DNA using thermophilic strand displacement amplification. Mol Cell Probes. Aug. 1996;10(4):247-56.
Stanford. HIV Drug resistance database. Available at https://hivdb.stanford.edu/pages/genotype-rx.html. Accessed on Oct. 10, 2016.
Tissen, P. Laboratory techniques in biochemistry and molecular biology:Hybridization with nucleic acid probes. Elsevier Science. 1993.
Tsaftaris A. et al. Rolling circle amplification of genomic templates for inverse PCR (RCA-GIP): a method for 5'- and 3'-genome walking without anchoring. Biotechnol Lett. Jan. 2010;32(1):157-61.
U.S. Appl. No. 15/780,370 Non-Final Office Action dated Jan. 10, 2023.

(56) References Cited

OTHER PUBLICATIONS

U.S. Appl. No. 15/780,370 Non-Final Office Action dated Nov. 26, 2021.
U.S. Appl. No. 16/434,941 Final Office Action dated Apr. 16, 2021.
U.S. Appl. No. 16/434,941 Non-Final Office Action dated Sep. 8, 2020.
U.S. Appl. No. 16/689,018 Non-Final Office Action dated Dec. 24, 2021.
U.S. Appl. No. 16/689,018 Notice of Allowance dated Sep. 28, 2023.
U.S. Appl. No. 16/945,553 Non-Final Office Action dated Dec. 22, 2021.
U.S. Appl. No. 16/434,941 Final Office Action dated Mar. 10, 2020.
U.S. Appl. No. 16/434,941 Office Action dated Nov. 25, 2019.
U.S. Appl. No. 15/780,370 Office Action dated Sep. 21, 2023.
U.S. Appl. No. 15/800,558 Office Action dated Jan. 26, 2018.
Walsh, et al. Chelex 100 as a medium for simple extraction of DNA for PCR-based typing from forensic material. BioTechniques. 1991;10(4):506-513.
Wang, et al., Using ultra-sensitive next generation sequencing to dissect DNA damage-induced mutagenesis. Nature:Scientific Report. Dec. 2015.6:25310.
Wang et al., DNA amplification method tolerant to sample degradation. Genome Research. 14(11):2357-2366 (2004).
Wharam, et al. Specific detection of DNA and RNA targets using a novel isothermal nucleic acid amplification assay based on the formation of a three-way junction structure. Nucleic Acids Res. Jun. 1, 2001; 29(11): e54.
Widlak et al. Cleavage Preferences of the Apoptotic Endonuclease DFF40 (Caspase-activated DNase or Nuclease) on Naked DNA and Chromatin Substrates. The Journal of Biological Chemistry 275:8226-8232 (2000).
Winzeler, et al. Functional Characterization of the *S. cerevisiae* Genome by Gene Deletion and Parallel Analysis. Science. Aug. 6, 1999: vol. 285, Issue 5429, pp. 901-906.
Yan, et al. Isothermal amplified detection of DNA and RNA. Mol Biosyst. May 2014;10(5):970-1003.
Zhang et al., "Amplification of target-specific, ligation-dependent circular probe" Gene (1998) 211:277-285.
Zhao et al.: Isothermal Amplification of Nucleic Acids. Chem Rev. 115(22):12491-12545 doi:10.1021/acs.chemrev.5b00428 (2015).
Mo et al., Cell-free Circulating miRNA Biomarkers in Cancer. Journal of Cancer, 3:432-448 (2012).
Thermostable FEN1, pp. 1-3. Printed on Jan. 20, 2024.

\* cited by examiner

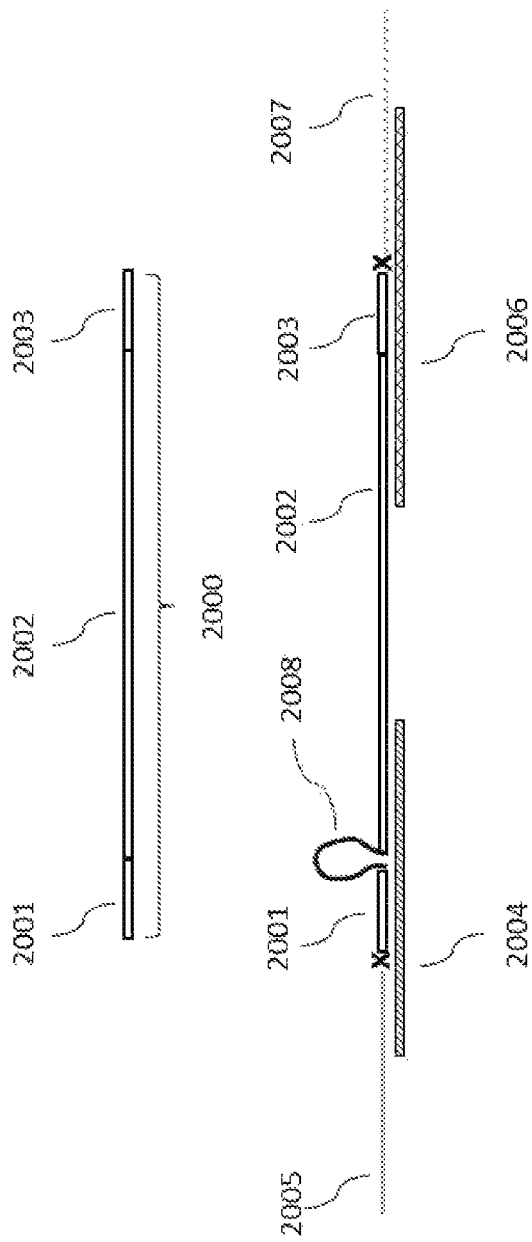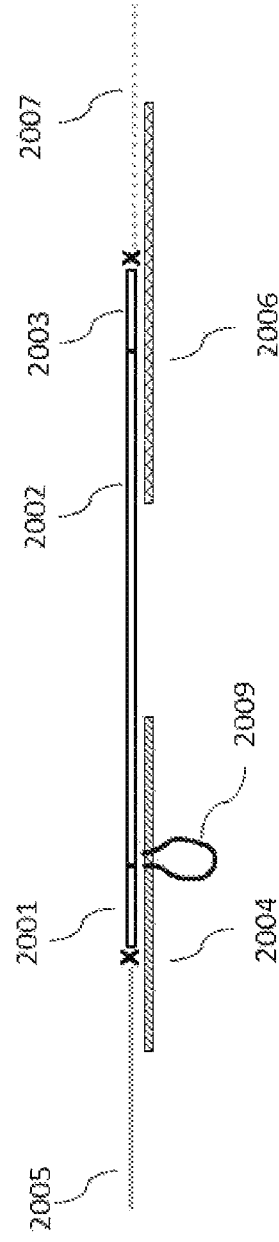
FIG. 2A
FIG. 2B

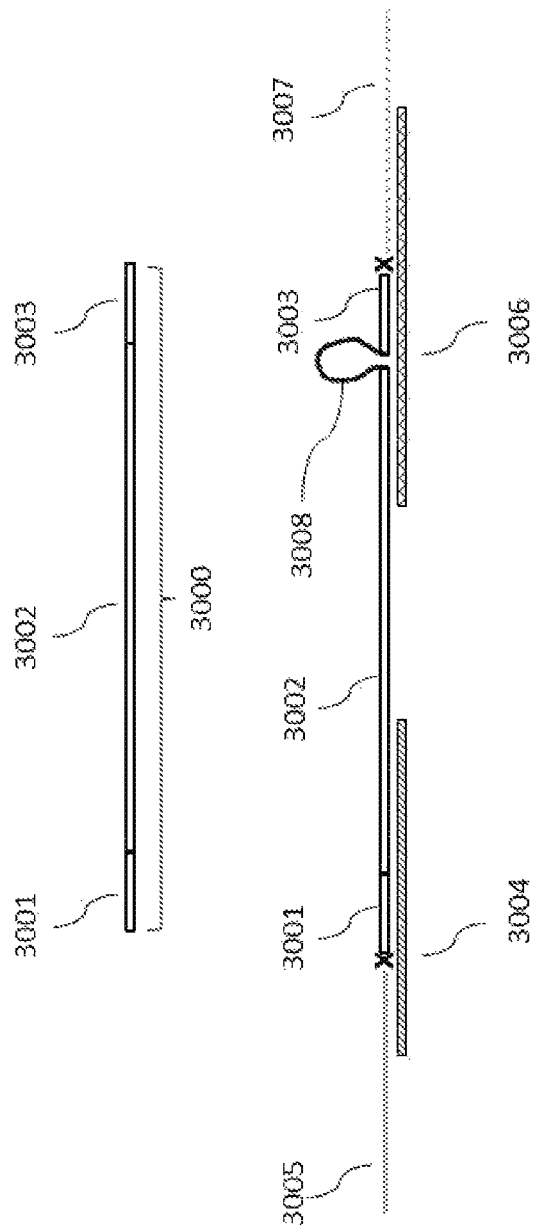
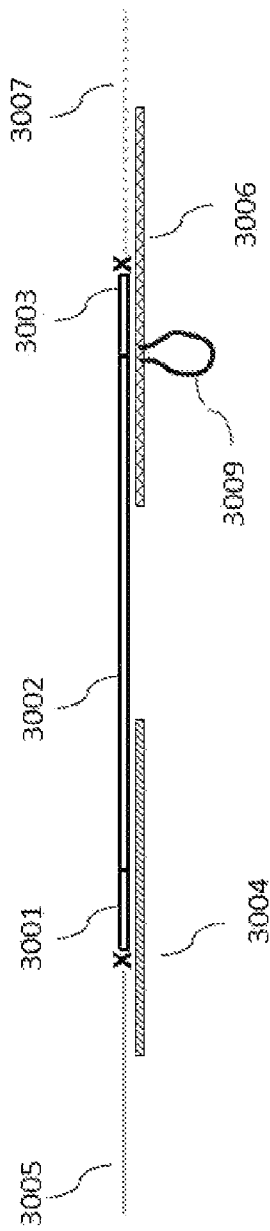
FIG. 3A
FIG. 3B

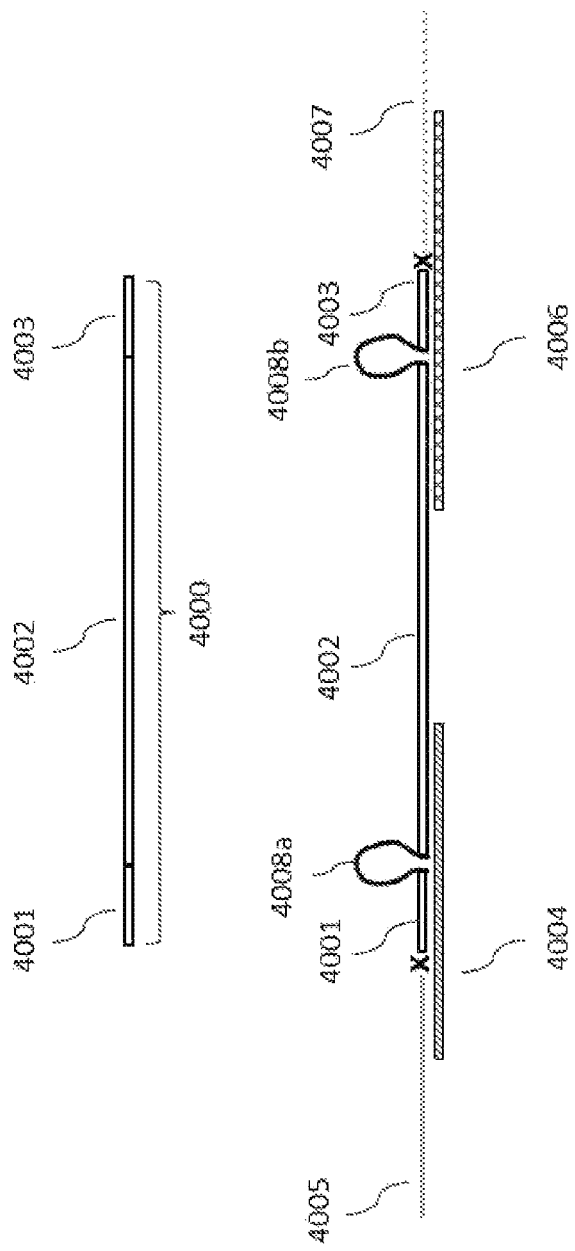

METHODS AND COMPOSITIONS FOR FORMING LIGATION PRODUCTS

CROSS REFERENCE TO RELATED APPLICATIONS

This application is the National Stage Entry of International Application No. PCT/US2019/036608, filed Jun. 11, 2019, which claims the benefit of U.S. Provisional Application No. 62/684,057, filed Jun. 12, 2018, the contents of each are incorporated herein by reference in their entirety for all purposes.

BACKGROUND OF THE INVENTION

Forming polynucleotide ligation products can have a variety of uses, such as examining target polynucleotides, molecular cloning methods to generate expression vectors, cDNA library construction, and as a pre-step to amplification and sequencing reactions. In many cases, target polynucleotides for analysis, molecular cloning, and other processes, are present in nucleic acid samples comprising a heterogeneous mixture of polynucleotides. Selectively forming ligation products comprising a target polynucleotide present in a heterogeneous mixture of polynucleotides may be preferred.

However, efficient ways of carrying out the selective formation of ligation products, for example with target polynucleotides comprising randomly fragment DNA such as cell-free DNA, are lacking. Existing methods for selectively forming ligation product can suffer from low efficiency, low yield, and cumbersome workflow.

SUMMARY OF THE INVENTION

In view of the foregoing, there is a need for improved methods in the generation of ligation products with single-stranded polynucleotide targets. The methods and compositions of the present disclosure address this need, and provide additional advantages as well.

In an aspect, the present disclosure provides a method for forming a ligation product comprising a single-stranded sample polynucleotide, wherein the single-stranded sample polynucleotide comprises a target polynucleotide joined to a first extension sequence at a 5' end of the target polynucleotide and to a second extension sequence at a 3' end of the target polynucleotide, the method comprising: (a) mixing the single-stranded sample polynucleotide, a first single-stranded adaptor, a second single-stranded adaptor, a first bridging probe, and a second bridging probe to form a polynucleotide complex, wherein said polynucleotide complex includes (i) a 5' end of the first bridging probe specifically hybridized to a 3' end of the first single-stranded adaptor via sequence complementarity, and a 5' end of the single-stranded sample polynucleotide specifically hybridized to a 3' end of the first bridging probe via sequence complementarity, and (ii) a 5' end of the second bridging probe specifically hybridized to a 3' end of the single-stranded sample polynucleotide via sequence complementarity, and a 5' end of the second single-stranded adaptor specifically hybridized to a 3' end of the second bridging probe via sequence complementarity; (b) ligating (i) the 3' end of the first single-stranded adaptor to the 5' end of the single-stranded sample polynucleotide and (ii) the 3' end of the single-stranded sample polynucleotide to the 5' end of the second single-stranded adaptor; and (c) degrading or selectively removing the first and second bridging probes, thereby forming the ligation product.

In some embodiments, the target polynucleotide comprises a cell-free DNA. In some embodiments, the cell-free DNA comprises a sequence variant. In some embodiments, the sequence variant comprises at least one of a single nucleotide polymorphism, a single nucleotide variant, an insertion, a deletion, a duplication, an inversion, a translocation, a copy number variation, a gene fusion, and a mutation indicative of methylation. In some embodiments, the target polynucleotide comprises a linear concatemer having at least one copy of a cell-free DNA sequence, or a complement thereof. In some embodiments, the target polynucleotide comprises genomic DNA or a fragment thereof.

In some embodiments, the first bridging probe hybridizes to at least a portion of the first extension sequence at the 5' end of the single-stranded sample polynucleotide. In some embodiments, the first bridging probe hybridizes to the first extension sequence and at least a portion of the target polynucleotide at the 5' end of the single-stranded sample polynucleotide. In some embodiments, a segment of the 5' end of the target polynucleotide does not specifically hybridize to the first bridging probe, and the segment forms a first single-stranded loop. In some embodiments, prior to ligating in (b), the first single-stranded loop is excised. In some cases, this loop is not excised. In some embodiments, a segment of the first bridging probe does not specifically hybridize to the 5' end of the target polynucleotide, and the segment forms a first single-stranded loop in the polynucleotide complex.

In some embodiments, the second bridging probe hybridizes to at least a portion of the second extension sequence at the 3' end of the single-stranded sample polynucleotide. In some embodiments, the second bridging probe hybridizes to the second extension sequence and at least a portion of the target polynucleotide at the 3' end of the single-stranded sample polynucleotide. In some embodiments, a segment of the 3' end of the target polynucleotide does not specifically hybridize to the second bridging probe, and the segment forms a second single-stranded loop. In some embodiments, prior to ligating in (b), the second single-stranded loop is excised. In some cases, this loop is not excised. In some embodiments, a segment of the second bridging probe does not specifically hybridize to the 3' end of the target polynucleotide, and the segment forms a second single-stranded loop in the polynucleotide complex.

In some embodiments, the first extension sequence comprises at least one of an amplification primer binding sequence, a sequencing primer binding sequence, a barcode sequence, and a molecular identifier sequence. In some embodiments, the second extension sequence comprises at least one of an amplification primer binding sequence, a sequencing primer binding sequence, a barcode sequence, and a molecular identifier sequence. In some embodiments, the first single-stranded adaptor comprises at least one of an amplification primer binding sequence, a sequencing primer binding sequence, a barcode sequence, and a molecular identifier sequence. In some embodiments, the second single-stranded adaptor comprises at least one of an amplification primer binding sequence, a sequencing primer binding sequence, a barcode sequence, and a molecular identifier sequence.

In some embodiments, the first bridging probe, the second bridging probe, or both the first and second bridging probes comprises modified nucleotides. In some embodiments, the first bridging probe, the second bridging probe, or both the first and second bridging probes comprises deoxyuridines.

In some embodiments, the first bridging probe, the second bridging probe, or both the first and second bridging probes comprising deoxyuridines comprises at least 5% deoxyuridines. In some embodiments, the first bridging probe, the second bridging probe, or both the first and second bridging probes comprising deoxyuridines comprises at least 5 deoxyuridines. In some embodiments, the first bridging probe, the second bridging probe, or both the first and second bridging probes comprises RNA.

In some embodiments, in (c), the first and second bridging probes are degraded. In some embodiments, the first and second bridging probes are degraded enzymatically or chemically. In some embodiments, degrading comprises treatment with an endonuclease or an exonuclease. In some embodiments, degrading comprises treatment with an RNA endonuclease or an RNA exonuclease. In some embodiments, degrading comprises treatment with an endonuclease and the endonuclease is uracil DNA glycosylase. In some embodiments, degrading comprises treatment with a chemical reagent. In some embodiments, the chemical reagent is sodium hydroxide.

In an aspect, the present disclosure provides a method for selectively ligating a first single-stranded adaptor and a second single-stranded adaptor to a single-stranded target sample polynucleotide in a reaction mixture comprising non-target sample polynucleotides, the single-stranded target sample polynucleotide comprising a target polynucleotide joined to a first extension sequence at a 5' end of the target polynucleotide and to a second extension sequence at a 3' end of the target polynucleotide, the method comprising: (a) ligating a first single-stranded adaptor to a 5' end of the single-stranded target sample polynucleotide, wherein a 5' end of a first bridging probe specifically hybridizes to a 3' end of the first single-stranded adaptor via sequence complementarity, and wherein a 3' end of the first bridging probe specifically hybridizes to a 5' end of the single-stranded target sample polynucleotide via sequence complementarity, wherein the 3' end of the first bridging probe does not specifically hybridize to a 5' end of non-target sample polynucleotides, and (b) ligating a second single-stranded adaptor to a 3' end of the single-stranded target sample polynucleotide, wherein a 5' end of a second bridging probe specifically hybridizes to a 3' end of the single-stranded target sample polynucleotide via sequence complementarity, and wherein a 3' end of the second bridging probe specifically hybridizes to a 5' end of the second single-stranded adaptor via sequence complementarity, wherein the 5' end of the second bridging probe does not specifically hybridize to a 3' end of non-target sample polynucleotides, thereby selectively ligating a first single-stranded adaptor and a second single-stranded adaptor to the single-stranded target sample polynucleotide.

In some embodiments, the target polynucleotide comprises a cell-free DNA. In some embodiments, the cell-free DNA comprises a sequence variant. In some embodiments, the sequence variant comprises at least one of a single nucleotide polymorphism, a single nucleotide variant, an insertion, a deletion, a duplication, an inversion, a translocation, a copy number variation, a gene fusion, and a mutation indicative of methylation. In some embodiments, the target polynucleotide comprises a linear concatemer having at least one copy of a cell-free DNA sequence, or a complement thereof. In some embodiments, the target polynucleotide comprises genomic DNA or a fragment thereof.

In some embodiments, the first bridging probes hybridizes to at least a portion of the first extension sequence at the 5' end of the single-stranded target sample polynucleotide. In some embodiments, the first bridging probes hybridizes to the first extension sequence and at least a portion of the target polynucleotide at the 5' end of the single-stranded target sample polynucleotide. In some embodiments, a segment of the 5' end of the target polynucleotide does not specifically hybridize to the first bridging probe, and the segment forms a first single-stranded loop. In some embodiments, prior to ligating in (a), the first single-stranded loop is excised. In some cases, this loop is not excised. In some embodiments, a segment of the first bridging probe does not specifically hybridize to the 5' end of the target polynucleotide, and the segment forms a first single-stranded loop in the polynucleotide complex.

In some embodiments, the second bridging probe hybridizes to at least a portion of the second extension sequence at the 3' end of the single-stranded target sample polynucleotide. In some embodiments, the second bridging probe hybridizes to the second extension sequence and at least a portion of the target polynucleotide at the 3' end of the single-stranded target sample polynucleotide. In some embodiments, a segment of the 3' end of the target polynucleotide does not specifically hybridize to the second bridging probe, and the segment forms a second single-stranded loop. In some embodiments, prior to ligating in (b), the second single-stranded loop is excised. In some cases, this loop is not excised. In some embodiments, a segment of the second bridging probe does not specifically hybridize to the 3' end of the target polynucleotide, and the segment forms a second single-stranded loop in the polynucleotide complex.

In some embodiments, the first bridging probe, the second bridging probe, or both the first and second bridging probes comprises modified nucleotides. In some embodiments, the first bridging probe, the second bridging probe, or both the first and second bridging probes comprises deoxyuridines. In some embodiments, the first bridging probe, the second bridging probe, or both the first and second bridging probes comprising deoxyuridines comprises at least 5% deoxyuridines. In some embodiments, the first bridging probe, the second bridging probe, or both the first and second bridging probes comprising deoxyuridines comprises at least 5 deoxyuridines. In some embodiments, the first bridging probe, the second bridging probe, or both the first and second bridging probes comprises RNA.

In some embodiments, the method further comprises degrading or selectively removing the first and second bridging probes. In some embodiments, the method further comprises degrading the first and second bridging probes. In some embodiments, the first and second bridging probes are degraded enzymatically or chemically. In some embodiments, the first and second bridging probes are degraded enzymatically and the degrading comprises treatment with an endonuclease or an exonuclease. In some embodiments, the first and second bridging probes are degraded enzymatically and the degrading comprises treatment with an RNA endonuclease or an RNA exonuclease. In some embodiments, degrading comprises treatment with an endonuclease and the endonuclease is a uracil DNA glycosylase. In some embodiments, the first and second bridging probes are degraded chemically and the degrading comprises treatment with a chemical reagent. In some embodiments, the chemical reagent is sodium hydroxide.

In some embodiments, the first extension sequence comprises at least one of an amplification primer binding sequence, a sequencing primer binding sequence, a barcode sequence, and a molecular identifier sequence. In some embodiments, the second extension sequence comprises at least one of an amplification primer binding sequence, a sequencing primer binding sequence, a barcode sequence, and a molecular identifier sequence. In some embodiments, the first single-stranded adaptor comprises at least one of an amplification primer binding sequence, a sequencing primer binding sequence, a barcode sequence, and a molecular identifier sequence. In some embodiments, the second single-stranded adaptor comprises at least one of an amplification primer binding sequence, a sequencing primer binding sequence, a barcode sequence, and a molecular identifier sequence.

In some embodiments, at least one of the first single-stranded adaptor and the second single-stranded adaptor comprises an amplification primer binding sequence. In some embodiments, the method further comprises generating a plurality of extension products. In some embodiments, generating the plurality of extension products comprises primer extension of a primer which hybridizes to the amplification primer binding sequence.

In an aspect, the present disclosure provides a reaction mixture for forming a ligation product comprising a single-stranded sample polynucleotide, wherein the single-stranded sample polynucleotide comprises a target polynucleotide joined to a first extension sequence at a 5' end of the target polynucleotide and to a second extension sequence at a 3' end of the target polynucleotide, comprising: (a) a mixture of the single-stranded sample polynucleotide, a first single-stranded adaptor, a second single-stranded adaptor, a first bridging probe, and a second bridging probe, wherein (i) a 5' end of the first bridging probe specifically hybridizes to a 3' end of the first single-stranded adaptor via sequence complementarity, and a 5' end of the single-stranded sample polynucleotide specifically hybridizes to a 3' end of the first bridging probe via sequence complementarity, and (ii) a 5' end of the second bridging probe specifically hybridizes to a 3' end of the single-stranded sample polynucleotide via sequence complementarity, and a 5' end of the second single-stranded adaptor specifically hybridizes to a 3' end of the second bridging probe via sequence complementarity; and (b) a ligase to effect (i) ligation of the 3' end of the first single-stranded adaptor to the 5' end of the single-stranded sample polynucleotide and (ii) ligation of the 3' end of the single-stranded sample polynucleotide to the 5' end of the second single-stranded adaptor.

In some embodiments, the target polynucleotide comprises cell-free DNA. In some embodiments, the cell-free DNA comprises a sequence variant. In some embodiments, the sequence variant comprises at least one of a single nucleotide polymorphism, a single nucleotide variant, an insertion, a deletion, a duplication, an inversion, a translocation, a copy number variation, a gene fusion, and a mutation indicative of methylation. In some embodiments, the target polynucleotide comprises a linear concatemer having at least one copy of a cell-free DNA sequence, or a complement thereof. In some embodiments, the target polynucleotide comprises genomic DNA or a fragment thereof.

In some embodiments, the first bridging probe hybridizes to at least a portion of the first extension sequence at the 5' end of the single-stranded sample polynucleotide. In some embodiments, the first bridging probes hybridizes to the first extension sequence and at least a portion of the target polynucleotide at the 5' end of the single-stranded sample polynucleotide. In some embodiments, a segment of the 5' end of the target polynucleotide does not specifically hybridize to the first bridging probe, and the segment forms a first single-stranded loop. In some embodiments, a segment of the first bridging probe does not specifically hybridize to the 5' end of the target polynucleotide, and the segment forms a first single-stranded loop in the polynucleotide complex.

In some embodiments, the second bridging probe hybridizes to at least a portion of the second extension sequence at the 3' end of the single-stranded sample polynucleotide. In some embodiments, the second bridging probe hybridizes to the second extension sequence and at least a portion of the target polynucleotide at the 3' end of the single-stranded sample polynucleotide. In some embodiments, a segment of the 3' end of the target polynucleotide does not specifically hybridize to the second bridging probe, and wherein the segment forms a second single-stranded loop. In some embodiments, a segment of the second bridging probe does not specifically hybridize to the 3' end of the target polynucleotide, and the segment forms a second single-stranded loop in the polynucleotide complex.

In some embodiments, the first extension sequence comprises at least one of an amplification primer binding sequence, a sequencing primer binding sequence, a barcode sequence, and a molecular identifier sequence. In some embodiments, the second extension sequence comprises at least one of an amplification primer binding sequence, a sequencing primer binding sequence, a barcode sequence, and a molecular identifier sequence. In some embodiments, the first single-stranded adaptor comprises at least one of an amplification primer binding sequence, a sequencing primer binding sequence, a barcode sequence, and a molecular identifier sequence. In some embodiments, the second single-stranded adaptor comprises at least one of an amplification primer binding sequence, a sequencing primer binding sequence, a barcode sequence, and a molecular identifier sequence.

In some embodiments, the first bridging probe, the second bridging probe, or both the first and second bridging probes comprises modified nucleotides. In some embodiments, the first bridging probe, the second bridging probe, or both the first and second bridging probes comprises deoxyuridines, ribonucleotides, or a combination thereof. In some embodiments, the first bridging probe, the second bridging probe, or both the first and second bridging probes comprises deoxyuridines. In some embodiments, the first bridging probe, the second bridging probe, or both the first and second bridging probes comprising deoxyuridines comprises at least 5% deoxyuridines. In some embodiments, the first bridging probe, the second bridging probe, or both the first and second bridging probes comprising deoxyuridines comprises at least 5 deoxyuridines. In some embodiments, the first bridging probe, the second bridging probe, or both the first and second bridging probes comprises RNA. In some embodiments, the first and second bridging probes are degradable. In some embodiments, the first and second bridging probes are degradable enzymatically or chemically.

In an aspect, the present disclosure provides a kit for generating a plurality of ligation products, an individual ligation product of the plurality comprising a single-stranded sample polynucleotide joined to first single-stranded adaptor and second single-stranded adaptor. In some embodiments, the kit comprises a plurality of first bridging probes, a plurality of second bridging probes, a plurality of first single-stranded adaptors, a plurality of second single-stranded adaptors, and instructions for using the plurality of first and second bridging probes for generating the plurality of ligation products, wherein: (a) a given first bridging probe comprises (i) a 5' end exhibiting sequence complementarity to a 3' end of a given first single-stranded adaptor, and (ii) a 3' end exhibiting sequence complementarity to a 5' end of a single-stranded sample polynucleotide; (b) a given second bridging probe comprises (i) a 5' end exhibiting sequence complementarity to a 3' end of the single-stranded sample polynucleotide, and (ii) a 3' end exhibiting sequence complementarity to a 5' end of a given second single-stranded adaptor; and (c) the single-stranded sample polynucleotide comprises a target polynucleotide joined to a first extension sequence at a 5' end of the target polynucleotide and to a second extension sequence at a 3' end of the target polynucleotide.

In some embodiments, the first bridging probe, the second bridging probe, or both the first and second bridging probes comprises deoxyuridines, ribonucleotides, or a combination thereof. In some embodiments, the kit further comprises a ligase enzyme. In some embodiments, the kit further comprises an endonuclease. In some embodiments, the kit further comprises an RNA endonuclease. In some embodiments, the endonuclease is uracil DNA-glycosylase. In some embodiments, the kit further comprises an exonuclease. In some embodiments, the kit further comprises an RNA exonuclease. In some embodiments, the kit further comprises sodium hydroxide. In some embodiments, the kit further comprises amplification primers capable of hybridizing to a portion of the first and/or second bridging primers, or a complement thereof. In some embodiments, the kit further comprises a polymerase.

In an aspect, the present disclosure provides a polynucleotide complex comprising a single-stranded target sample polynucleotide, a first single-stranded adaptor, a second-single stranded adaptor, a first bridging probe, and a second bridging probe, the single-stranded target sample polynucleotide comprising a target polynucleotide joined to a first extension sequence at a 5' end of the target polynucleotide and to a second extension sequence at a 3' end of the target polynucleotide, wherein (i) a 5' end of the first bridging probe specifically hybridizes to a 3' end of the first single-stranded adaptor via sequence complementarity, and a 5' end of the single-stranded target sample polynucleotide specifically hybridizes to a 3' end of the first bridging probe via sequence complementarity, and (ii) a 5' end of the second bridging probe specifically hybridizes to a 3' end of the single-stranded target sample polynucleotide via sequence complementarity, and a 5' end of the second single-stranded adaptor specifically hybridizes to a 3' end of the second bridging probe via sequence complementarity. In some embodiments, the first bridging probe, the second bridging probe, or both the first and second bridging probes comprises at least 5 deoxyuridines.

In an aspect, the present disclosure provides a method of preparing a plurality of ligation products comprising single-stranded target sample polynucleotides for sequencing without performing solid-phase based enrichment of the single-stranded target sample polynucleotides, wherein a single-stranded target sample polynucleotide comprises a target polynucleotide joined to a first extension sequence at a 5' end of the target polynucleotide and to a second extension sequence at a 3' end of the target polynucleotide, comprising: (a) providing a plurality of ligation products, wherein an individual ligation product of the plurality is generated by: (i) mixing a single-stranded target sample polynucleotide, a first single-stranded adaptor, a second single-stranded adaptor, a first bridging probe, and a second bridging probe to form a polynucleotide complex, the polynucleotide complex includes (a) a 5' end of the first bridging probe specifically hybridized to a 3' end of the first single-stranded adaptor via sequence complementarity, and a 5' end of the single-stranded target sample polynucleotide specifically hybridized to a 3' end of the first bridging probe via sequence complementarity, and (b) a 5' end of the second bridging probe specifically hybridized to a 3' end of the single-stranded sample polynucleotide via sequence complementarity, and a 5' end of the second single-stranded adaptor specifically hybridized to a 3' end of the second bridging probe via sequence complementarity, (ii) ligating (a) the 3' end of the first single-stranded adaptor to the 5' end of the single-stranded sample polynucleotide and (b) the 3' end of the single-stranded sample polynucleotide to the 5' end of the second single-stranded adaptor, and (iii) degrading or selectively removing the first and second bridging probes, thereby forming the ligation product; and optionally (b) subjecting the plurality of ligation products, or amplification products thereof, to a sequencing reaction. In some embodiments, (i)-(iii) of (a) occurs in a single reaction mixture. In some embodiments, (i)-(iii) of (a) are performed without altering a concentration of the single-stranded target sample polynucleotides in the reaction mixture.

In an aspect, the present disclosure provides a method for forming a ligation product comprising a single-stranded sample polynucleotide, wherein the single-stranded sample polynucleotide comprises a target polynucleotide joined to an extension sequence at a 5' end of the target polynucleotide, the method comprising: (a) mixing the single-stranded sample polynucleotide, a single-stranded adaptor, and a bridging probe to form a polynucleotide complex, wherein the polynucleotide complex includes (i) a 5' end of the bridging probe specifically hybridized to a 3' end of the first single-stranded adaptor via sequence complementarity, and (ii) a 3' end of the bridging probe specifically hybridized to the extension sequence and at least a portion of the target polynucleotide via sequence complementarity, wherein the extension sequence exhibits complete sequence complementarity to a portion of the bridging probe; (b) ligating the 3' end of the single-stranded adaptor to the 5' end of the single-stranded sample polynucleotide; and (c) degrading or selectively removing the bridging probe, thereby forming the ligation product.

In an aspect, the present disclosure provides a method for forming a ligation product comprising a single-stranded sample polynucleotide, wherein the single-stranded sample polynucleotide comprises a target polynucleotide joined to an extension sequence at a 3' end of the target polynucleotide, the method comprising: (a) mixing the single-stranded sample polynucleotide, a single-stranded adaptor, and a bridging probe to form a polynucleotide complex, wherein the polynucleotide complex includes (i) a 5' end of the bridging probe specifically hybridized to the extension sequence and at least a portion of the target polynucleotide via sequence complementarity, wherein the extension sequence exhibits complete sequence complementarity to a portion of the bridging probe, and (ii) a 3' end of the bridging probe specifically hybridized to a 5' end of the single-stranded adaptor via sequence complementarity; (b) ligating the 3' end of the single-stranded sample polynucleotide to the 5' end of the single-stranded adaptor; and (c) degrading or selectively removing the bridging probe, thereby forming the ligation product.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A and 2B provide illustrations of a polynucleotide complex having a first single-stranded loop.

FIGS. 3A and 3B provide illustrations of a polynucleotide complex having a second single-stranded loop.

FIGS. 4A and 4B provide illustrations of a polynucleotide complex having both a first single-stranded loop and a second single-stranded loop.

DETAILED DESCRIPTION OF THE INVENTION

Figure 1:
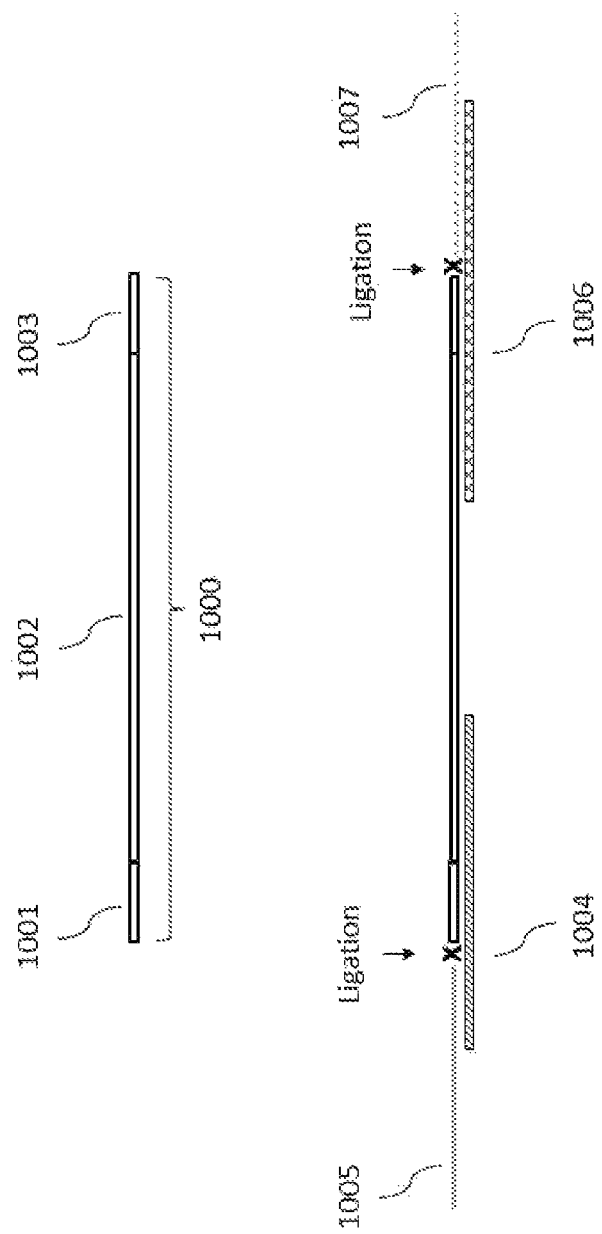
FIG. 1 illustrates the formation of a ligation product comprising a single-stranded sample polynucleotide, a first single-stranded adaptor, and a second single-stranded adaptor.

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide," "nucleic acid," and "oligonucleotide" are used interchangeably. As used herein, they generally refer to a polymeric form of nucleotides of any length, either deoxyribonucleotides or ribonucleotides, or analogs thereof. Polynucleotides may have any three dimensional structure, and may perform any function, known or unknown. Non-limiting examples of polynucleotides are coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adaptors, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

With reference to polynucleotides, the term "a 5' end," as used herein, refers to a portion of a polynucleotide that is 5' with respect to a reference point on the polynucleotide (when considered in a 5' to 3' direction). In some embodiments, the reference point used with term "a 5' end" comprises the 3' terminal nucleotide. Similarly, the term "a 3' end," as used herein, generally refers to a portion of a polynucleotide that is 3' with respect to a reference point on the polynucleotide (when considered in a 5' to 3' direction). In some embodiments, the reference point used with the term "a 3' end" comprises the 5' terminal nucleotide.

The term "sample polynucleotide," as used herein, refers to a polynucleotide to which adaptors (e.g., first and second single-stranded adaptors) are to be attached. In some embodiments, a sample polynucleotide, e.g., a single-stranded sample polynucleotide, comprises a target polynucleotide joined to extension sequences.

The term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target polynucleotide may be a portion of a larger polynucleotide (e.g. a sample polynucleotide). In general, the term "target sequence" refers to a nucleic acid sequence on a single strand of nucleic acid. The target sequence may be a portion of a gene, a regulatory sequence, genomic DNA, cDNA, fusion gene, RNA including mRNA, miRNA, rRNA, or others. The target sequence may be a target sequence from a sample or a secondary target such as a product of an amplification reaction.

The term "sequence variant," as used herein, refers to any variation in sequence relative to one or more reference sequences. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous.

The term "bridging probe," as used herein, refers to a polynucleotide that interacts with one or more polynucleotides, for example by hybridization. A bridging probe can hybridize, partially or completely, to one or more single-stranded sample polynucleotides and one or more adaptor polynucleotides. Any proportion of the hybridized region can be complementary. Thus, a bridging probe is hybridizable to one or more polynucleotides. A bridging probe may comprise one or more modified nucleotides, such as methylated nucleotides and nucleotide analogs. A bridging probe may be further modified, such as by conjugation with a labeling component, tag, reactive moiety, or binding partner.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters. In some embodiments, a bridging probe specifically hybridizes to a specified target sequence via complementarity between a pre-determined, non-random sequence of the bridging probe and the target sequence.

The terms "ligate" and "ligation," as used herein, refer to any enzymatic or non-enzymatic process by which an inter-nucleotide linkage is formed between two polynucleotide ends, which ends optionally are adjacently hybridized to a template. For example, the ends of DNA fragments can be ligated by forming a phosphodiester bond between the 3'-hydroxyl of one DNA terminus with the 5'-phosphoryl of another. In some cases, the inter-nucleotide linkage can be formed between two polynucleotide fragments (intermolecular). In some cases, the inter-nucleotide linkage can be formed between two terminal ends (5' end and 3' end) of a single fragment (intramolecular). Terminal ends of RNA fragments can similarly be joined by the formation of a phosphodiester bond. Polynucleotides that can be ligated may either be single-stranded or double-stranded. Double-stranded nucleic acids can comprise staggered ends, overhangs, or sticky ends where there are unpaired nucleotides at the 3' or 5' end of the DNA or RNA molecule. Double-stranded nucleic acids can comprise blunt ends, where the end nucleotides are paired at the 3' or 5' end of the DNA or RNA molecule. Ligation can comprise use of an enzyme, such as a ligase enzyme.

The term "adaptor," as used herein, generally refers to a nucleic acid which can be attached to another polynucleotide. For example, an adaptor can refer to a single-stranded polynucleotide which can be attached to a single-stranded polynucleotide (e.g., a cell-free polynucleotide, fragment of a cell-free polynucleotide, genomic DNA, or fragment of genomic DNA). In some cases, an adaptor can refer to a double-stranded nucleic acid which can be attached to a double-stranded nucleic acid. An adaptor can be attached to either a 5' end or a 3' end of a polynucleotide. In some cases, an adaptor can be attached to both ends of a polynucleotide, that is, one adaptor to each end.

The term "ligation product", as used herein, generally refers to a product resulting from a ligation reaction. In some cases, ligation product can refer to a DNA polynucleotide resulting from the ligation of two DNA polynucleotides. In some cases, ligation product can refer to a circular DNA polynucleotide resulting from the ligation of two ends of a linear DNA polynucleotide. In some cases, ligation product can refer to a RNA polynucleotide resulting from the ligation of two RNA polynucleotides. In some cases, ligation product can refer to a circular RNA polynucleotide resulting from the ligation of two ends of a linear RNA polynucleotide. In some cases, ligation product can refer to the polynucleotide product resulting from the ligation of a DNA polynucleotide and an RNA polynucleotide.

The terms "amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation. In some cases, the amplification is effected by means of PCR using a pair of primers. Amplified products can be subjected to subsequence analyses, including but not limited to melting curve analysis, nucleotide sequencing, single-strand conformation polymorphism assay, allele-specific oligonucleotide hybridization, Southern blot analysis, and restriction endonuclease digestion.

The terms "isolated" and "isolating," with reference to a polynucleotide or polynucleotide complex, including but not limited to ligation products and amplification products, generally refers to a preparation of the substance (e.g., polynucleotide, polynucleotide complex, ligation products and amplification products thereof) devoid of at least some of the other components that may also be present where the substance or a similar substance naturally occurs or is initially obtained from (e.g., a biological sample, a sample reaction volume, e.g., a ligation reaction volume, an amplification reaction volume etc). For example, an isolated substance may be prepared using a purification technique to enrich it from a source mixture. Enrichment can be measured on an absolute basis or in terms of a concentration, for example in terms of weight per volume of solution, molecules per volume of solution, or any other appropriate measure.

The term "support," as used herein, generally refers to a substance having a surface on which another species can be immobilized. Non-limiting examples of supports include a particle (e.g., a bead), a surface of a well, a surface of a vessel, a solid surface, a planar surface, a surface of an array, a porous surface (e.g., a micro-cavity of a porous surface), a resin (e.g., a resin in a column) and a fiber (e.g., a fiber in a membrane or support). Moreover, a support can comprise any suitable material with non-limiting examples that include a metal, a metal oxide, carbonaceous materials and polymeric species. A support having a selective binding agent immobilized thereto may be used to, for example, isolate or enrich a species such as polynucleotide or polynucleotide complex comprising a tag which specifically binds the binding agent.

In various aspects, the present disclosure provides methods, compositions, reaction mixtures, kits, and systems for producing ligation products using at least one bridging probe. Ligation products of the present disclosure can be further processed and analyzed using nucleic acid analysis methods, for example, sequencing to identify a sequence variant. In some embodiments, the methods are useful for generating ligation products comprising polynucleotides, e.g., target polynucleotides, including but not limited to, cell-free DNA and genomic DNA. Various aspects of the disclosure provide ligation products useful for downstream analysis, including but not limited to sequencing analysis and sequence variant identification.

Existing methods of generating ligation products may include one or more enrichment steps, wherein target polynucleotides are selected from a heterogeneous nucleic acid sample prior to adaptor ligation. Enrichment steps may be employed for a variety of reasons. In some cases, target enrichment is utilized to obtain target polynucleotides from a heterogeneous sample in which the target polynucleotides represent a small fraction of the sample (e.g., present in low abundance). In some cases, a nucleic acid sample contains a plurality of different polynucleotides which are not desired for further processing, e.g., sequencing. By enriching for target polynucleotides, improvements in time- and cost-efficiency, for example in sequencing analysis, may be realized.

Existing enrichment methods include solid-phase based techniques. Solid-phase based techniques include methods wherein an oligonucleotide exhibiting sequence complementarity to a target sequence is immobilized on a solid-support, non-limiting examples of which include a bead or other surface, e.g., an array surface. Target polynucleotides exhibiting sequence complementarity to the oligonucleotide can hybridize to the oligonucleotide attached to the support, and the hybridized target polynucleotides can be isolated from other polynucleotides present in a sample via the support. For example, a support can comprise a magnetic bead which can be collected by a magnet. For further example, a support can comprise a bead attached to a tag which can be collected by binding the tag to a binding partner. The yield from such solid-phase enrichment methods can, in some cases, be low, for example in cases where a target polynucleotide is present in low abundance. One or more washing steps for separating a solid support with target polynucleotides hybridized thereto from non-target polynucleotides of a sample can decrease the recovery of the target polynucleotides. In view of the foregoing, there is a need for improved methods for generating ligation products comprising target polynucleotides, such as methods not including solid-phase based target enrichment steps.

In an aspect, the present disclosure provides a method for forming a ligation product comprising a single-stranded sample polynucleotide, wherein the single-stranded sample polynucleotide comprises a target polynucleotide joined to an extension sequence at a 5' end of the target polynucleotide. In some embodiments, the method comprises: (a) mixing the single-stranded sample polynucleotide, a single-stranded adaptor, and a bridging probe to form a polynucleotide complex, wherein the polynucleotide complex includes (i) a 5' end of the bridging probe specifically hybridized to a 3' end of first single-stranded adaptor via sequence complementarity, and (ii) a 3' end of the bridging probe specifically hybridized to the extension sequence and at least a portion of the target polynucleotide via sequence complementarity, wherein the extension sequence exhibits complete sequence complementarity to a portion of the bridging probe; (b) ligating the 3' end of the single-stranded adaptor to the 5' end of the single-stranded sample polynucleotide; and (c) degrading or selectively removing the bridging probe, thereby forming the ligation product. In some embodiments, the hybridized portion comprising the bridging probe and the target polynucleotide includes at least one nucleotide mismatch. In some embodiments, the entire target polynucleotide is hybridized to the bridging probe. In some embodiments, the hybridized portion comprising the bridging probe and the entire target polynucleotide includes at least one nucleotide mismatch.

In an aspect, the present disclosure provides a method for forming a ligation product comprising a single-stranded sample polynucleotide, wherein the single-stranded sample polynucleotide comprises a target polynucleotide joined to an extension sequence at a 3' end of the target polynucleotide. In some embodiments, the method comprises: (a) mixing the single-stranded sample polynucleotide, a single-stranded adaptor, and a bridging probe to form a polynucleotide complex, wherein the polynucleotide complex includes (i) a 5' end of the bridging probe specifically hybridized to the extension sequence and at least a portion of the target polynucleotide via sequence complementarity, wherein the extension sequence exhibits complete sequence complementarity to a portion of the bridging probe, and (ii) a 3' end of the bridging probe specifically hybridized to a 5' end of the single-stranded adaptor via sequence complementarity; (b) ligating the 3' end of the single-stranded sample polynucleotide to the 5' end of the single-stranded adaptor; and (c) degrading or selectively removing the bridging probe, thereby forming the ligation product. In some embodiments, the hybridized portion comprising the bridging probe and the target polynucleotide includes at least one nucleotide mismatch. In some embodiments, the entire target polynucleotide is hybridized to the bridging probe. In some embodiments, the hybridized portion comprising the bridging probe and the entire target polynucleotide includes at least one nucleotide mismatch.

In an aspect, the present disclosure provides a method for forming a ligation product comprising a single-stranded sample polynucleotide, wherein the single-stranded sample polynucleotide comprises a target polynucleotide joined to a first extension sequence at a 5' end of the target polynucleotide and to a second extension sequence at a 3' end of the target polynucleotide. In some embodiments, the method comprises: (a) mixing the single-stranded sample polynucleotide, a first single-stranded adaptor, a second single-stranded adaptor, a first bridging probe, and a second bridging probe to form a polynucleotide complex, wherein the polynucleotide complex includes (i) a 5' end of the first bridging probe specifically hybridized to a 3' end of the first single-stranded adaptor via sequence complementarity, and a 5' end of the single-stranded sample polynucleotide specifically hybridized to a 3' end of the first bridging probe via sequence complementarity, and (ii) a 5' end of the second bridging probe specifically hybridized to a 3' end of the single-stranded sample polynucleotide via sequence complementarity, and a 5' end of the second single-stranded adaptor specifically hybridized to a 3' end of the second bridging probe with via sequence complementarity; (b) ligating (i) the 3' end of the first single-stranded adaptor to the 5' end of the single-stranded sample polynucleotide and (ii) the 3' end of the single-stranded sample polynucleotide to the 5' end of the second single-stranded adaptor; and (c) degrading or selectively removing the first and second bridging probes, thereby forming the ligation product.

A single-stranded sample polynucleotide can comprise a target polynucleotide joined to a first extension sequence at the 5' end of the target polynucleotide and to a second extension sequence at the 3' end of the target polynucleotide. In some embodiments, the target polynucleotide comprises a cell-fee polynucleotide, for example a cell-free DNA polynucleotide (e.g., cell-free DNA), genomic DNA, or complements thereof. In some embodiments, the target polynucleotide comprising a cell-free DNA, genomic DNA, or complements thereof, comprises a sequence variant. The sequence variant can comprise at least one of a single nucleotide polymorphism, a single nucleotide variant, an insertion, a deletion, a duplication, an inversion, a translocation, a copy number variation, a gene fusion, and a mutation indicative of methylation. In some embodiments, the target polynucleotide comprises a linear concatemer having at least one copy of a cell-free DNA sequence or a complement thereof. In some embodiments, the target polynucleotide comprises a linear concatemer having at least one copy of a fragment of genomic DNA or a complement thereof.

A linear concatemer can be generated, for example, by rolling circle amplification of a circularized cell-free DNA polynucleotide or a circularized fragment of genomic DNA. In some embodiments, the target polynucleotide comprises a polynucleotide produced from whole genome amplification. A variety of techniques are available for generating linear concatemers and for conducting whole genome amplification, non-limiting examples of which include polymerase chain reaction (PCR) and isothermal primer extension.

Single-stranded sample polynucleotides comprising a target polynucleotide joined to a first extension sequence at the 5' end of the target polynucleotide can be generated by joining at least one adaptor comprising the extension sequence to the 5' end of the target polynucleotide. Adaptors can be joined to a target polynucleotide, for example, via ligation. Single-stranded sample polynucleotides comprising a target polynucleotide joined to a second extension sequence at the 3' end of the target polynucleotide can be similarly generated by joining at least one adaptor comprising the extension sequence to the 3' end of the target polynucleotide. The extension sequence joined to the 5' end and/or the 3' end of a target polynucleotide can comprise a variety of sequence elements, including but not limited to, one or more sequences exhibiting sequence complementarity to a bridging probe or a portion thereof, one or more amplification primer annealing sequences, a complement thereof, or a portion thereof, one or more sequencing primer annealing sequences, a complement thereof, or a portion thereof, one or more barcode sequences, a complement thereof, or a portion thereof, one or more common sequences shared among multiple different adaptors or subsets of different adaptors; one or more restriction enzyme recognition sites or a portion thereof; one or more overhangs complementary to one or more target polynucleotide overhangs; one or more probe binding sites (e.g., for attachment to a sequencing platform, such as a flow cell for massive parallel sequencing, such as flow cells as developed by Illumina, Inc.) or a portion thereof, one or more random or near-random sequences (e.g., one or more nucleotides selected at random from a set of two or more different nucleotides at one or more positions, with each of the different nucleotides selected at one or more positions represented in a pool of adaptors comprising the random sequence) or a portion thereof, and any combination thereof.

FIG. 1 provides an illustrative example of a ligation product comprising a single-stranded sample polynucleotide generated according to embodiments of methods herein. A single-stranded sample polynucleotide 1000 comprises a first extension sequence 1001 and a second extension sequence 1003 joined to a target polynucleotide 1002. When mixed with bridging probes (1004 and 1006) and single-stranded adaptors (1005 and 1007), the single-stranded sample polynucleotide 1000 forms a polynucleotide complex, wherein the first single-stranded adaptor 1005 hybridizes to a 5' end of a first bridging probe 1004, a 3' end of the first bridging probe 1004 hybridizes to a 5' end of the single-stranded sample polynucleotide 1000, a 3' end of the single-stranded sample polynucleotide 1000 hybridizes to a 5' end of a second bridging probe 1006, and a 3' end of the second bridging probe 1006 hybridizes to a 5' end of the second single-stranded adaptor 1007. A ligation product can be formed by ligating the 3' end of the first single-stranded adaptor 1005 to the 5' end of the single-stranded sample polynucleotide 1000 and ligating the 3' end of the single-stranded sample polynucleotide 1000 to the 5' end of the second single-stranded adaptor 1007.

Forming a polynucleotide complex comprising a single-stranded sample polynucleotide, a first single-stranded adaptor, a second single-stranded adaptor, a first bridging probe, and a second bridging probe can depend on the length (in nucleotides) of the hybridized portions (e.g., specifically hybridized), the degree of sequence complementarity between the hybridized portions (e.g. specifically hybridized), and the temperature at which the mixing is conducted. The length of any one of the hybridized portions (e.g., first single-stranded adaptor hybridized to the first bridging probe, first bridging probe hybridized to the single-stranded sample polynucleotide, the single-stranded sample polynucleotide hybridized to the second bridging probe, and the second bridging probe hybridized to the second single-stranded adaptor) can be any suitable length, such as at least 20 base pairs (e.g., at least 25, 30, 35, 50, 100, 150, 200, 250, 300, 350, 400, 450, or 500 base pairs or more than 500 base pairs) in length, any portion of which may be complementary. The length of any one of the hybridized portions can be any suitable length, such as between 5-500 base pairs (e.g. between 10-450 base pairs, 30-400 base pairs, 30-300 base pairs, 30-200 base pairs, 30-100 base pairs, or 30-50 base pairs) in length, any portion of which may be complementary. In some embodiments, any one of the hybridized portions is at least 60% complementary (e.g. at least 70%, 75%, 80%, 85%, 90%, or 95% complementary or more than 95% complementary) when optimally aligned. In some embodiments, any one of the hybridized portions is between 50%-100% complementary (e.g., between 60%-90%, 60%-80%, or 60%-70% complementary) when optimally aligned.

The length of the hybridized portion comprising a 3' end of the first single-stranded adaptor and a 5' end of the first bridging probe can be any suitable length, such as at least 20 base pairs (e.g. at least 25, 30, 35, 50, 100, 150, 200, 250, 300, 350, 400, 450, or 500 base pairs or more than 500 base pairs) in length, any portion of which may be complementary. The length of the hybridized portion comprising a 3' end of the first single-stranded adaptor and a 5' end of the first bridging probe can be any suitable length, such as between 5-500 base pairs (e.g. between 10-450 base pairs, 30-400 base pairs, 30-300 base pairs, 30-200 base pairs, 30-100 base pairs, or 30-50 base pairs) in length, any portion of which may be complementary. In some embodiments, the hybridized portion is at least 60% complementary (e.g. at least 70%, 75%, 80%, 85%, 90%, or 95% complementary or more than 95% complementary) when optimally aligned. In some embodiments, the hybridized portion is between 50%-100% complementary (e.g. between 60%-90%, 60%-80%, or 60%-70% complementary) when optimally aligned.

The length of the hybridized portion comprising a 3' end of the first bridging probe and a 5' end of the single-stranded sample polynucleotide can be any suitable length, such as at least 20 base pairs (e.g. at least 25, 30, 35, 50, 100, 150, 200, 250, 300, 350, 400, 450, or 500 base pairs or more than 500 base pairs) in length, any portion of which may be complementary. The length of the hybridized portion comprising a 3' end of the first bridging probe and a 5' end of the single-stranded sample polynucleotide can be any suitable length, such as between 5-500 base pairs (e.g. between 10-450 base pairs, 30-400 base pairs, 30-300 base pairs, 30-200 base pairs, 30-100 base pairs, or 30-50 base pairs) in length, any portion of which may be complementary. In some embodiments, the hybridized portion is at least 60% complementary (e.g. at least 70%, 75%, 80%, 85%, 90%, or 95% complementary or more than 95% complementary) when optimally aligned. In some embodiments, the hybridized portion is between 50%-100% complementary (e.g. between 60%-90%, 60%-80%, or 60%-70% complementary) when optimally aligned.

The length of the hybridized portion comprising a 3' end of the single-stranded sample polynucleotide and a 5' end of the second bridging probe can be any suitable length, such as at least 20 base pairs (e.g. at least 20, 25, 30, 35, 50, 100, 150, 200, 250, 300, 350, 400, 450, or 500 base pairs or more than 500 base pairs) in length, any portion of which may be complementary. The length of the hybridized portion comprising a 3' end of the single-stranded sample polynucleotide and a 5' end of the second single-stranded bridging probe can be any suitable length, such as between 5-500 base pairs (e.g. between 10-450 base pairs, 30-400 base pairs, 30-300 base pairs, 30-200 base pairs, 30-100 base pairs, or 30-50 base pairs) in length, any portion of which may be complementary. In some embodiments, the hybridized portion is at least 60% complementary (e.g. at least 70%, 75%, 80%, 85%, 90%, or 95% complementary or more than 95% complementary) when optimally aligned. In some embodiments, the hybridized portion is between 50%-100% complementary (e.g. between 60%-90%, 60%-80%, or 60%-70% complementary) when optimally aligned.

The length of the hybridized portion comprising a 3' end of the second bridging probe and a 5' end of the second single-stranded adaptor can be any suitable length, such as at least 20 base pairs (e.g. at least 20, 25, 30, 35, 50, 100, 150, 200, 250, 300, 350, 400, 450, or 500 base pairs or more than 500 base pairs) in length, any portion of which may be complementary. The length of the hybridized portion comprising a 3' end of the second single-stranded bridging probe and a 5' end of the second single-stranded adaptor can be any suitable length, such as between 5-500 base pairs (e.g. between 10-450 base pairs, 30-400 base pairs, 30-300 base pairs, 30-200 base pairs, 30-100 base pairs, or 30-50 base pairs) in length, any portion of which may be complementary. In some embodiments, the hybridized portion is at least 60% complementary (e.g. at least 70%, 75%, 80%, 85%, 90%, or 95% complementary or more than 95% complementary) when optimally aligned. In some embodiments, the hybridized portion is between 50%-100% complementary (e.g. between 60%-90%, 60%-80%, or 60%-70% complementary) when optimally aligned.

The formation of a complex of polynucleotides can also depend on the temperature of the mixture relative to the melting temperature of the hybridized regions. Melting temperature, also referred to as Tm, generally represents the temperature at which 50% of an oligonucleotide consisting of a reference sequence (which may in fact be a subsequence within a larger polynucleotide) and its complementary sequence are hybridized (or separated). Tm may be based on a standard calculation, algorithm, or measurement, available in the art. An example tool for measuring Tm, OligoAnalyzer, is made available by Integrated DNA Technologies at www.idtdna.com/calc/analyzer, which may be set to use default parameters. Other similar tools are available. In some embodiments, a polynucleotide complex forms when the temperature of the mixture is within $\pm 15°$ C. of the Tm of the hybridized region comprising the single-stranded sample polynucleotide and the first bridging probe or within $\pm 15°$ C. of the Tm of the hybridized region comprising the single-stranded sample polynucleotide and the second bridging probe. In some embodiments, formation for a complex of polynucleotides is affected by other mixture conditions, including but not limited to buffer components and concentrations.

In some embodiments, the first bridging probe hybridizes to at least a portion of the first extension sequence joined to the 5' end of a target polynucleotide. In some embodiments, the first bridging probe hybridizes to the entire first extension sequence and at least a portion of the target polynucleotide at the 5' end of the single-stranded sample polynucleotide, as illustrated in FIG. 1.

In some embodiments, a segment of the 5' end of the target polynucleotide does not specifically hybridize to the first bridging probe, for example due to lack of sequence complementarity, and the segment forms a first single-stranded loop in the polynucleotide complex (e.g., the loop is formed in the single-stranded sample polynucleotide). In some embodiments, the first single-stranded loop is excised prior to the ligating in (b). In some embodiments, the first single-stranded loop is excised concurrently with the ligating in (b). The first single-stranded loop can be excised, for example, by an enzyme with nuclease activity. However, in some cases, this loop is not excised. In some embodiments, a segment of the first bridging probe does not specifically hybridize to the 5' end of the target polynucleotide, for example due to lack of sequence complementarity, and the segment forms a first single-stranded loop in the polynucleotide complex (e.g., the loop is formed in the first bridging probe).

FIG. 2A provides an illustrative example of a first single-stranded loop in a polynucleotide complex. A single-stranded sample polynucleotide 2000 comprises a first extension sequence 2001 and a second extension sequence 2003 joined to a target polynucleotide 2002. A polynucleotide complex comprises a 3' end of a first single-stranded adaptor 2005 hybridized to a 5' end of a first bridging probe 2004, a 3' end of the first bridging probe 2004 hybridized to the 5' end of the sample polynucleotide 2000, including a portion of the target polynucleotide 2002, a 5' end of a second single-stranded adaptor 2006 hybridized to the 3' end of the sample polynucleotide 2000, including a portion of the target polynucleotide 2002, and a 5' end of a second single-stranded adaptor 2007 hybridized to a 3' end of the second bridging probe 2006. A segment of the 5' end of the target polynucleotide 2002 does not specifically hybridize to the first bridging probe 2004, for example due to lack of sequence complementarity, and the segment forms a first single-stranded loop 2008. As illustrated in FIG. 2B, a first single-stranded loop 2009 may be formed in the first bridging probe 2004.

In some embodiments, the second bridging probe hybridizes to at least a portion of the second extension sequence joined to the 3' end of the target polynucleotide. In some embodiments, the second bridging probe hybridizes to the entire second extension sequence and at least a portion of the target polynucleotide at the 3' end of the single-stranded sample polynucleotide, as illustrated in FIG. 1.

In some embodiments, a segment of the 3' end of the target polynucleotide does not specifically hybridize to the second bridging probe, for example due to lack of sequence complementarity, and the segment forms a second single-stranded loop in the polynucleotide complex. In some embodiments, the second single-stranded loop is excised prior to the ligating in (b). In some embodiments, the second single-stranded loop is excised concurrently with the ligating in (b). The second single-stranded loop can be excised, for example, by an enzyme with nuclease activity. However, in some cases, this loop is not excised. In some embodiments, a segment of the second bridging probe does not specifically hybridize to the 3' end of the target polynucleotide, for example due to lack of sequence complementarity, and the segment forms a second single-stranded loop in the polynucleotide complex (e.g., the loop is formed in the second bridging probe).

FIG. 3 provides an illustrative example of a second single-stranded loop in a polynucleotide complex. A single-stranded sample polynucleotide 3000 comprises a first extension sequence 3001 and a second extension sequence 3003 joined to a target polynucleotide 3002. A polynucleotide complex comprises a 3' end of a first single-stranded adaptor 3005 hybridized to a 5' end of a first bridging probe 3004, a 3' end of the first bridging probe 3004 hybridized to a 5' end of the single-stranded sample polynucleotide 3000, including a portion of the target polynucleotide 3002, a 5' end of a second single-stranded adaptor 3006 hybridized to a 3' end of the single-stranded sample polynucleotide 3000, including a portion of the target polynucleotide 3002, and a 3' end of the second bridging probe 3006 hybridized to a 5' end of a second single-stranded adaptor 3007. A segment of the 3' end of the target polynucleotide 3002 does not specifically hybridize to the second bridging probe 3006, for example due to lack of sequence complementarity, and the segment forms a second single-stranded loop 3008. As illustrated in FIG. 3B, a second single-stranded loop 3009 may be formed in the second bridging probe 3006.

In some embodiments, as illustrated in FIG. 4A, a first single-stranded loop and a second single-stranded loop are both formed in a polynucleotide complex. A single-stranded sample polynucleotide 4000 comprises a first extension sequence 4001 and a second extension sequence 4003 joined to a target polynucleotide 4002. A polynucleotide complex comprises a first single-stranded adaptor 4005 hybridized to a first bridging probe 4004, the first bridging probe 4004 hybridized to the single-stranded sample polynucleotide 4000, including a portion of the target polynucleotide 4002, a second single-stranded adaptor 4006 hybridized to the single-stranded sample polynucleotide 4000, including a portion of the target polynucleotide 4002, and a second single-stranded adaptor 4007 hybridized to the second bridging probe 4006. A segment of the 5' end of the target polynucleotide 4002 does not specifically hybridize to the first bridging probe 4004, for example due to lack of sequence complementarity, and the segment forms a first single-stranded loop 4008a. A segment of the 3' end of the target polynucleotide 4002 does not specifically hybridize to the second bridging probe 4006, for example due to lack of sequence complementarity, and the segment forms a second single-stranded loop 4008b. The first single-stranded loop and the second single-stranded loop can be excised before the ligating in (a) and/or (b). As illustrated in FIG. 4B, a polynucleotide complex may comprise a first single-stranded loop 4009a in the first bridging probe 4004 and a second single-stranded loop 4009b in the second bridging probe.

The ligation product can be formed by ligating (i) the 3' end of the first single-stranded adaptor polynucleotide to the 5' end of the single-stranded sample polynucleotide and (ii) the 3' end of the second single-stranded sample polynucleotide to the 5' end of the second single-stranded adaptor. A ligation product can be formed by ligating a terminal nucleotide at the 3' end of the first single-stranded adaptor to a terminal nucleotide at the 5' end of the single-stranded sample polynucleotide and ligating a terminal nucleotide at the 3' end of the single-stranded sample polynucleotide to a terminal nucleotide at the 5' end of the second single-stranded adaptor. Ligating the terminal ends can comprise use of an enzyme, such as a ligase enzyme. A variety of ligase enzymes useful in the subject methods are available, non-limiting examples of which are provided herein.

In some cases, single-stranded sample polynucleotides comprising desired target polynucleotides are enriched from a heterogeneous population of sample polynucleotides prior to adaptor ligation. Enriching for sample polynucleotides comprising desired target polynucleotides may be performed so that adaptors can be preferentially ligated to target sample polynucleotides, or those which have a desired target polynucleotide sequence. Using the methods provided herein, adaptors can be preferentially ligated to target sample polynucleotides without the need for such enrichment steps. A first bridging probe having a sequence hybridizable to at least a portion of the target polynucleotide can be used to preferentially ligate a first single-stranded adaptor to a sample polynucleotide comprising a target polynucleotide compared to sample polynucleotides comprising non-target polynucleotides, or polynucleotides having a nucleic acid sequences which are not desired to be analyzed. A second bridging probe having a sequence hybridizable to at least a portion of the target polynucleotide can be used to preferentially ligate a second single-stranded adaptor to a sample polynucleotide comprising a target polynucleotide compared to sample polynucleotides comprising non-target polynucleotides, or polynucleotides having nucleic acid sequences which are not desired to be analyzed. When using first and second bridging probes to ligate first and single-stranded adaptor polynucleotides to single-stranded sample polynucleotides, enrichment steps including, but not limited to, solid-phased based enrichment of sample polynucleotides can be omitted.

In some embodiments, at least one of the bridging probes comprises a double-stranded nucleic acid and prior to forming a polynucleotide complex, the double-stranded nucleic acid is separated into two single-stranded polynucleotides. In some embodiments, one of the two single-stranded polynucleotides functions as a bridging probe. In some embodiments, both of the two single-stranded polynucleotides function as bridging probes. A double-stranded nucleic acid can be separated, for example, by heat denaturation or melting.

In some embodiments, a bridging probe (e.g., a first bridging probe, a second bridging probe) comprises nucleotides such as deoxyribonucleotides, ribonucleotides, and combinations thereof. In some embodiments, a bridging probe comprises one or more modified nucleotides, such as methylated nucleotides and nucleotide analogs. In some embodiments, a bridging probe comprises one modified nucleotide. In some embodiments, a bridging probe comprises at least one modified nucleotide (e.g. at least 2, 5, 10, 15, 20, 30, 40, 50 modified nucleotides or more than 50 modified nucleotides). In some embodiments, a bridging probe comprises at least 1% modified nucleotides (e.g. at least 2%, 3%, 4%, 5%, 6%, 7%, 8%, 9%, 10% modified nucleotides or more than 10% modified nucleotides). In some embodiments, a bridging probe comprises between 10% and 100% modified nucleotides (e.g. between 20% and 90% modified nucleotides, between 30% and 80% modified nucleotides, or between 40% and 70% modified nucleotides). In some embodiments, a bridging probe comprises deoxyuridines. In some embodiments, a bridging probe comprises at least 1 deoxyuridine (e.g. at least 2, 5, 10, 20, 30 deoxyuridines or more than 30 deoxyuridines). In some embodiments, a bridging probe comprising deoxyuridines comprises at least 1% deoxyuridines (e.g. at least 2%, 3%, 4%, 5%, 6%, 7%, 8%, 9%, 10% deoxyuridines or more than 10% deoxyuridines). In some embodiments, a bridging probe comprises between 5% and 50% deoxyuridines. In some embodiments, a bridging probe comprises RNA.

In some embodiments, a bridging probe (e.g., a first bridging probe, a second bridging probe) is degraded or selectively removed concurrently with or after formation of a ligation product. Preferably, degradation or removal occurs after ligation. In some embodiments, degrading a bridging probe comprises degrading the bridging probe enzymatically or chemically. In some embodiments, a bridging probe is degraded enzymatically by a nuclease, an endonuclease, an exonuclease, and/or a ribonuclease, including endoribonucleases and exoribonucleases. In some embodiments, the degradation is effected by an endonuclease (e.g. DNA endonuclease, RNA endonuclease). In some embodiments, a single-stranded sample polynucleotide, a first single-stranded adaptor, and a second single-stranded adaptor comprise DNA while the bridging probe(s) comprises RNA. In such cases, an RNA endonuclease that cleaves RNA (such as RNase H, which cleaves RNA in an RNA-DNA duplex) can be used to selectively degrade the RNA bridging probe(s) and not the single-stranded sample polynucleotide, the first single-stranded adaptor, and the second single-stranded adaptor. In some embodiments, an RNA exonuclease can be used. In some embodiments, a single-stranded sample polynucleotide, a first single-stranded adaptor and a second single-stranded adaptor comprise RNA while the bridging probe(s) comprises DNA. Use of a DNA endonuclease that cleaves DNA can selectively degrade the DNA bridging probe(s) and not the single-stranded RNA polynucleotides. In some embodiments, a bridging probe comprises one or more deoxyuridines, and the bridging probe is degraded by a uracil DNA-glycosylase. A variety of endonuclease enzymes useful in the subject methods are available, non-limiting examples of which are provided herein. In some embodiments, the bridging probe is degraded chemically. Chemical degradation can be effected by chemical agents that degrade RNA such as sodium hydroxide; or chemical agents that degrade DNA such as natural antibiotics (e.g. bleomycin, neocarzinostatin) or synthetic reagents (e.g. methidiumpropyl-EDTA iron(II) complexes).

In some embodiments, a bridging probe comprises a tag, and the bridging probe is selectively removed with a binding element that selectively binds the tag. In some embodiments, the tag is biotin. Where selectively removing a bridging probe comprising a biotin tag is desired, a binding element comprising avidin or modified avidin can be used.

In some embodiments, a complex of polynucleotides is isolated from a sample volume prior to degradation or selective removal of a bridging probe (e.g., a first bridging probe, a second bridging probe). The complex of polynucleotides can be isolated to yield a sample preparation substantially free of reagents such as, but not limited to, unhybridized polynucleotides including single-stranded sample polynucleotides, first single-stranded adaptors, and second single-stranded adaptors; enzymes such as ligase and nucleases; and reagents including salts and other ions. By "substantially free" is meant that at least 50% (e.g., at least 60%, 70%, 80%, 90% or greater) of the starting amount is removed or not present in the sample preparation. A complex of polynucleotides can be isolated from a sample volume by immobilizing it directly or indirectly to a support comprising a selective binding agent that specifically binds a tag attached to the bridging probe. A support may comprise a particle, a surface of a well, a surface of a vessel, a solid surface, a planar surface, a surface of an array, a porous surface (e.g., a micro-cavity of a porous surface), a resin (e.g., a resin in a column) and a fiber (e.g., a fiber in a membrane or support). In some embodiments, the support is a particle such as a bead, for example a magnetic bead. In some embodiments, the support is a resin such as a resin loaded into a purification column. Supports for isolating a complex of polynucleotides may have immobilized onto it a selective binding agent which can specifically interact with a tag, such as a tag attached to a bridging probe. For example, polynucleotide complexes can be isolated from the sample reaction volume by selectively binding a tag attached to a bridging probe of a polynucleotide complex to a selective binding agent, e.g., a binding agent immobilized to a support, and using the support to then remove the polynucleotide complexes from the sample solution. In this way, the polynucleotide complexes can be isolated from unligated polynucleotides prior to additional sample preparation steps.

As previously described, a first single-stranded adaptor comprises a segment which hybridizes to a portion of a first bridging probe. In addition to the segment which hybridizes to the bridging probe, the first single-stranded adaptor can comprise at least one additional segment located 5' of the portion which hybridizes to the first bridging probe (e.g., upstream), and the at least one additional segment does not specifically hybridize to the bridging probe via sequence complementarity. The at least one additional segment of a first single-stranded adaptor which does not specifically hybridize to a bridging probe can comprise one or more amplification primer annealing sequences, a complement thereof, or a portion thereof, one or more sequencing primer annealing sequences, a complement thereof, or a portion thereof, one or more barcode sequences, or a portion thereof, one or more common sequences shared among multiple different adaptors or subsets of different adaptors; one or more restriction enzyme recognition sites, or a portion thereof, one or more overhangs complementary to one or more target polynucleotide overhangs; one or more probe binding sites (e.g., for attachment to a sequencing platform, such as a flow cell for massive parallel sequencing, such as flow cells as developed by Illumina, Inc.); one or more random or near-random sequences (e.g., one or more nucleotides selected at random from a set of two or more different nucleotides at one or more positions, with each of the different nucleotides selected at one or more positions represented in a pool of adaptors comprising the random sequence); and any combination thereof. Where multiple ligation products are generated in parallel from multiple single-stranded sample polynucleotides, a portion of the at least one additional segment of the first single-stranded adaptor may have a nucleic acid sequence identical to that of other ligation products generated.

As previously described, a second single-stranded adaptor comprises a segment which hybridizes to a portion of a second bridging probe. In addition to the segment which hybridizes to the bridging probe, the second single-stranded adaptor can comprise at least one additional segment located 3' of the portion which hybridizes to the second bridging probe (e.g., downstream), and the at least one additional segment does not specifically hybridize to the bridging probe via sequence complementarity. The at least one additional segment of a second single-stranded adaptor which does not specifically hybridize to a bridging probe can comprise one or more amplification primer annealing sequences, a complement thereof, or a portion thereof, one or more sequencing primer annealing sequences, a complement thereof, or a portion thereof, one or more barcode sequences, or a portion thereof, one or more common sequences shared among multiple different adaptors or subsets of different adaptors; one or more restriction enzyme recognition sites, or a portion thereof, one or more overhangs complementary to one or more target polynucleotide overhangs; one or more probe binding sites (e.g., for attachment to a sequencing platform, such as a flow cell for massive parallel sequencing, such as flow cells as developed by Illumina, Inc.); one or more random or near-random sequences (e.g., one or more nucleotides selected at random from a set of two or more different nucleotides at one or more positions, with each of the different nucleotides selected at one or more positions represented in a pool of adaptors comprising the random sequence); and any combination thereof. Where multiple ligation products are generated in parallel from multiple single-stranded sample polynucleotides, a portion of the at least one additional segment of the second single-stranded adaptor may have a nucleic acid sequence identical to that of other ligation products generated.

The additional segments of the first and second single-stranded adaptors can be of any suitable length. In some embodiments, the additional segment of the first single-stranded adaptor is at least 5, 10, 15, 20, 25, 30, 40, 50, or more nucleotides in length (e.g. between 5-30 or between 10-20 nucleotides in length). In some embodiments, the additional segment of the second single-stranded adaptor is at least 5, 10, 15, 20, 25, 30, 40, 50, or more nucleotides in length (e.g. between 5-30 or between 10-20 nucleotides in length).

The additional segments of the first and/or second single-stranded adaptors can be used in latter processing of ligation products, including but not limited to amplification reactions and sequencing reactions for sequence analysis. For example, the at least one additional segment of a plurality of different first single-stranded adaptors can comprise one or more amplification primer annealing sequences, a complement thereof, or a portion thereof which can be used in the amplification of ligation products. An amplification primer annealing sequence shared amongst a plurality of ligation products enables the parallel amplification of the plurality of ligation products using the same amplification primers. The additional segments of the first and second single-stranded adaptors can comprise a probe binding site or a sequencing adaptor. A sequencing adaptor generally refers to oligonucleotides incorporated at the 5' and/or 3' ends of polynucleotides to facilitate one or more steps of a polynucleotide sequencing reaction. In some embodiments, a sequencing adaptor is used to bind a polynucleotide comprising the sequencing adaptor to a flow cell for next generation sequencing. Non-limiting examples of next-generation sequencing methods are single-molecule real-time sequencing, ion semiconductor sequencing, pyrosequencing, sequencing by synthesis, sequencing by ligation, and chain termination. Sequencing adaptors for flow cell attachment may comprise any suitable sequence compatible with next generation sequencing systems, e.g. 454 Sequencing, Ion Torrent Proton or PGM, and Illumina X10. Non-limiting examples of sequencing adaptors for next generation sequencing methods include P5 and P7 adaptors suitable for use with Illumina sequencing systems; TruSeq Universal Adapter; and TruSeq Indexed Adapter. In some embodiments, a sequencing adaptor is used to enrich for polynucleotides comprising the adaptor sequence, such as via amplification (e.g. by polymerase chain reaction (PCR)). A sequencing adaptor may also comprise a barcode and/or sample index sequence.

In some embodiments, the additional segment of the first single-stranded adaptor and/or the second single-stranded adaptor comprises a barcode sequence. In some embodiments, the barcode sequence is not the same for all first single-stranded adaptors and/or second single-stranded adaptors in a reaction and the barcode sequences can be used to distinguish a ligation product from a plurality of ligation products. A barcode sequence can refer to a known nucleic acid sequence that allows some feature of a polynucleotide with which the barcode is associated to be identified. Barcodes can each have a length within a range of 4 to 35 nucleotides, 6 to 30 nucleotides, or 8 to 20 nucleotides. In some embodiments, barcodes are at least 3, 4, 5, 6, 7, 8, 9, 10, 11, 12, 13, 14, or 15 nucleotides or more in length. In some embodiments, barcodes are less than 6 nucleotides in length. In some embodiments, barcodes associated with some target polynucleotides are a different length than barcodes associated with other target polynucleotides. The melting temperatures of barcodes within a set can be within ±10° C. of one another, within ±5° C. of one another, or within ±2° C. of one another. Barcodes can be members of a minimally cross-hybridizing set. For example, the nucleotide sequence of each member of such a set can be sufficiently different from that of every other member of the set such that no member can form a stable duplex with the complement of any other member under moderate or stringent hybridization conditions. The nucleotide sequence of each member of a minimally cross-hybridizing set can differ from those of every other member by at least two nucleotides. In some embodiments, the barcode sequence of each first single-stranded adaptors in a single reaction is different from every other barcode sequence. In some embodiments, the barcode sequence is uniquely associated with a single ligation reaction in a plurality of ligation reactions. In some embodiments, the barcode sequence of each second single-stranded adaptors in a single reaction is different from every other barcode sequence.

In an aspect, the present disclosure provides a method for selectively ligating a first single-stranded adaptor and a second single-stranded adaptor to a single-stranded target sample polynucleotide in a reaction mixture comprising non-target sample polynucleotides, the single-stranded target sample polynucleotide comprising a target polynucleotide joined to a first extension sequence at a 5' end of the target polynucleotide and to a second extension sequence at a 3' end of the target polynucleotide. The method comprises (a) ligating a first single-stranded adaptor to a 5' end of the single-stranded target sample polynucleotide, wherein a 5' end of a first bridging probe specifically hybridizes to a 3' end of the first single-stranded adaptor via sequence complementarity, and wherein a 3' end of the first bridging probe specifically hybridizes to a 5' end of the single-stranded sample polynucleotide via sequence complementarity, wherein the 3' end of the first bridging probe does not specifically hybridize to a 5' end of non-target sample polynucleotides, and (b) ligating a second single-stranded adaptor to a 3' end of the single-stranded sample polynucleotide, wherein a 5' end of a second bridging probe specifically hybridizes to a 3' end of the single-stranded sample polynucleotide via sequencing complementarity, and wherein a 3' end of the second bridging probe specifically hybridizes to a 5' end of the second single-stranded adaptor via sequence complementarity, wherein the 5' end of the second bridging probe does not specifically hybridize to a 3' end of non-target sample polynucleotides, thereby selectively ligating a first single-stranded adaptor and a second single-stranded adaptor to the single-stranded target sample polynucleotide.

A given single-stranded sample polynucleotide of the nucleic acid sample comprises a target polynucleotide joined to a first extension sequence at the 5' end of the target polynucleotide and to a second extension sequence at the 3' end of the target polynucleotide, as described elsewhere herein. In some embodiments, the target polynucleotide comprises a cell-fee polynucleotide, for example a cell-free DNA polynucleotide (e.g., cell-free DNA), genomic DNA, or complements thereof. In some embodiments, the target polynucleotide comprising a cell-free DNA, genomic DNA, or complements thereof, comprises a sequence variant. The sequence variant can comprise at least one of a single nucleotide polymorphism, a single nucleotide variant, an insertion, a deletion, a duplication, an inversion, a translocation, a copy number variation, a gene fusion, and a mutation indicative of methylation. In some embodiments, the target polynucleotide comprises a linear concatemer having at least one copy of a cell-free DNA sequence or a complement thereof. In some embodiments, the target polynucleotide comprises a linear concatemer having at least one copy of a fragment of genomic DNA or a complement thereof.

The extension sequence joined to the 5' end and/or at the 3' end of a target polynucleotide can comprise a variety of sequence elements, including but not limited to, one or more sequences exhibiting sequence complementarity to a bridging probe or a portion thereof, one or more amplification primer annealing sequences, a complement thereof, or a portion thereof, one or more sequencing primer annealing sequences, a complement thereof, or a portion thereof, one or more barcode sequences, a complement thereof, or a portion thereof, one or more common sequences shared among multiple different adaptors or subsets of different adaptors; one or more restriction enzyme recognition sites or a portion thereof, one or more overhangs complementary to one or more target polynucleotide overhangs; one or more probe binding sites (e.g., for attachment to a sequencing platform, such as a flow cell for massive parallel sequencing, such as flow cells as developed by Illumina, Inc.) or a portion thereof, one or more random or near-random sequences (e.g., one or more nucleotides selected at random from a set of two or more different nucleotides at one or more positions, with each of the different nucleotides selected at one or more positions represented in a pool of adaptors comprising the random sequence) or a portion thereof, and any combination thereof.

As described elsewhere herein, the first bridging probe can hybridize to at least a portion of the first extension sequence joined to the 5' end of the single-stranded target sample polynucleotide. In some embodiments, the first bridging probe hybridizes to the entire first extension sequence and at least a portion of the target polynucleotide at the 5' end of the single-stranded target sample polynucleotide. In some embodiments, the 3' end of the first bridging probe does not specifically hybridize to a 5' end of non-target sample polynucleotides, and the formation of polynucleotide complexes comprising non-target sample polynucleotides can be minimized. In some embodiments, a segment of the 5' end of the target polynucleotide does not specifically hybridize to the first bridging probe, for example due to lack of sequence complementarity, and the segment forms a first single-stranded loop. In some embodiments, the first single-stranded loop is excised prior to ligating the first single-stranded adaptor to the single-stranded target sample polynucleotide. In some embodiments, the first single-stranded loop is excised concurrently with ligating the first single-stranded adaptor to the single-stranded target sample polynucleotide. The first single-stranded loop can be excised, for example, by an enzyme with nuclease activity. However, in some cases, this loop is not excised. In some embodiments, a segment of the first bridging probe does not specifically hybridize to the 5' end of the target polynucleotide, for example due to lack of sequence complementarity, and the segment forms a first single-stranded loop (e.g., the loop is formed in the first bridging probe).

As described elsewhere herein, the second bridging probe can hybridize to at least a portion of the second extension sequence joined to the 3' end of the single-stranded target sample polynucleotide. In some embodiments, the second bridging probe hybridizes to the entire second extension sequence and at least a portion of the target polynucleotide at the 3' end of the single-stranded target sample polynucleotide. In some embodiments, the 5' end of the second bridging probe does not specifically hybridize to a 3' end of non-target sample polynucleotides, and the formation of polynucleotide complexes comprising non-target sample polynucleotides can be minimized. In some embodiments, a segment of the 3' end of the target polynucleotide does not specifically hybridize to the second bridging probe, for example due to lack of sequence complementarity, and the segment forms a second single-stranded loop. In some embodiments, the second single-stranded loop is excised prior to ligating the single-stranded target sample polynucleotide to the second single-stranded adaptor. In some embodiments, the second single-stranded loop is excised concurrently with ligating the single-stranded target sample polynucleotide to the second single-stranded adaptor. The second single-stranded loop can be excised, for example, by an enzyme with nuclease activity. However, in some cases, this loop is not excised. In some embodiments, a segment of the second bridging probe does not specifically hybridize to the 3' end of the target polynucleotide, for example due to lack of sequence complementarity, and the segment forms a second single-stranded loop (e.g., the loop is formed in the second bridging probe).

As previously described, using first and second bridging probes in methods and compositions herein allows for the selective or preferential ligation of adaptors to target sample polynucleotides in a sample comprising non-target sample polynucleotides. In some embodiments, using first and second bridging probes in methods provided herein, which methods do not include an enrichment step (e.g., a solid-phase based enrichment step), yields a plurality of ligation products in which the desired ligation product represents at least 50% of the total (e.g., at least 60%, 70%, 80%, 90%, 95% or greater).

In some embodiments, at least one of the bridging probes comprises a double-stranded nucleic acid and the double-stranded nucleic acid is separated into two single-stranded polynucleotides prior to forming the ligation product. In some embodiments, one of the two single-stranded polynucleotides functions as a bridging probe. In some embodiments, both of the two single-stranded polynucleotides function as bridging probes. A double-stranded nucleic acid can be separated, for example, by heat denaturation or melting.

In some embodiments, a bridging probe (e.g., a first bridging probe, a second bridging probe) comprises nucleotides such as deoxyribonucleotides, ribonucleotides, deoxyuridines, and combinations thereof. In some embodiments, a bridging probe comprises one or more modified nucleotides, such as methylated nucleotides and nucleotide analogs. In some embodiments, a bridging probe comprises one modified nucleotide. In some embodiments, a bridging probe comprises at least one modified nucleotide (e.g. at least 2, 5, 10, 15, 20, 30, 40, 50 modified nucleotides or more than 50 modified nucleotides). In some embodiments, a bridging probe comprises at least 1% modified nucleotides (e.g. at least 2%, 3%, 4%, 5%, 6%, 7%, 8%, 9%, 10% modified nucleotides or more than 10% modified nucleotides). In some embodiments, a bridging probe comprises between 10% and 100% modified nucleotides (e.g. between 20% and 90% modified nucleotides, between 30% and 80% modified nucleotides, or between 40% and 70% modified nucleotides). In some embodiments, a bridging probe comprises deoxyuridines. In some embodiments, a bridging probe comprises at least 1 deoxyuridine (e.g. at least 2, 5, 10, 20, 30 deoxyuridines or more than 30 deoxyuridines). In some embodiments, a bridging probe comprising deoxyuridines comprises at least 1% deoxyuridines (e.g. at least 2%, 3%, 4%, 5%, 6%, 7%, 8%, 9%, 10% deoxyuridines or more than 10% deoxyuridines). In some embodiments, a bridging probe comprises between 5% and 50% deoxyuridines. In some embodiments, a bridging probe comprises RNA.

In some embodiments, a bridging probe (e.g., a first bridging probe, a second bridging probe) is degraded or selectively removed concurrently with or after formation of a ligation product. Preferably, degradation or removal occurs after ligation. In some embodiments, degrading a bridging probe comprises degrading the bridging probe enzymatically or chemically. In some embodiments, a bridging probe is degraded enzymatically by a nuclease, an endonuclease, an exonuclease, and/or a ribonuclease, including endoribonucleases and exoribonucleases. In some embodiments, the degradation is effected by an endonuclease (e.g. DNA endonuclease, RNA endonuclease). In some embodiments, a single-stranded target sample polynucleotide, a first single-stranded adaptor, and a second single-stranded adaptor comprise DNA while the bridging probe(s) comprises RNA. In such cases, an RNA endonuclease that cleaves RNA (such as RNase H, which cleaves RNA in an RNA-DNA duplex) can be used to selectively degrade the RNA bridging probe(s) and not the single-stranded target sample polynucleotide, the first single-stranded adaptor, and the second single-stranded adaptor. In some cases, an RNA exonuclease can be used. In some embodiments, a single-stranded target sample polynucleotide, a first single-stranded adaptor and a second single-stranded adaptor comprise RNA while the bridging probe(s) comprises DNA. Use of a DNA endonuclease that cleaves DNA can selectively degrade the DNA bridging probe(s) and not the single-stranded RNA polynucleotides. In some embodiments, a bridging probe comprises one or more deoxyuridines, and the bridging probe is degraded by a uracil DNA-glycosylase. A variety of endonuclease enzymes useful in the subject methods are available, non-limiting examples of which are provided herein.

In some embodiments, the bridging probe is degraded chemically. Chemical degradation can be effected by chemical agents that degrade RNA such as sodium hydroxide; or chemical agents that degrade DNA such as natural antibiotics (e.g. bleomycin, neocarzinostatin) or synthetic reagents (e.g. methidiumpropyl-EDTA iron(II) complexes).

In some embodiments, a bridging probe comprises a tag, and the bridging probe is selectively removed with a binding element that selectively binds the tag. As previously described, the tag can be biotin. Where selectively removing a bridging probe comprising a biotin tag is desired, a binding element comprising avidin or modified avidin can be used.

As previously described, a first single-stranded adaptor comprises a segment which hybridizes to a portion of a first bridging probe. In addition to the segment which hybridizes to the bridging probe, the first single-stranded adaptor can comprise at least one additional segment located 5' of the portion which hybridizes to the first bridging probe (e.g., upstream), and the at least one additional segment does not specifically hybridize to the bridging probe via sequence complementarity. The at least one additional segment of a first single-stranded adaptor which does not specifically hybridize to a bridging probe can comprise one or more amplification primer annealing sequences, a complement thereof, or a portion thereof, one or more sequencing primer annealing sequences, a complement thereof, or a portion thereof, one or more barcode sequences, or a portion thereof, one or more common sequences shared among multiple different adaptors or subsets of different adaptors; one or more restriction enzyme recognition sites, or a portion thereof; one or more overhangs complementary to one or more target polynucleotide overhangs; one or more probe binding sites (e.g., for attachment to a sequencing platform, such as a flow cell for massive parallel sequencing, such as flow cells as developed by Illumina, Inc.); one or more random or near-random sequences (e.g., one or more nucleotides selected at random from a set of two or more different nucleotides at one or more positions, with each of the different nucleotides selected at one or more positions represented in a pool of adaptors comprising the random sequence); and any combination thereof. Where multiple ligation products are generated in parallel from multiple single-stranded target sample polynucleotides, a portion of the at least one additional segment of the first single-stranded adaptor may have a nucleic acid sequence identical to that of other ligation products generated.

As previously described, a second single-stranded adaptor comprises a segment which hybridizes to a portion of a second bridging probe. In addition to the segment which hybridizes to the second bridging probe, the second single-stranded adaptor can comprise at least one additional segment located 3' of the portion which hybridizes to the second bridging probe (e.g., downstream), and the at least one additional segment does not specifically hybridize to the bridging probe via sequence complementarity. The at least one additional segment of a second single-stranded adaptor which does not specifically hybridize to a bridging probe can comprise one or more amplification primer annealing sequences, a complement thereof, or a portion thereof; one or more sequencing primer annealing sequences, a complement thereof, or a portion thereof; one or more barcode sequences, or a portion thereof; one or more common sequences shared among multiple different adaptors or subsets of different adaptors; one or more restriction enzyme recognition sites, or a portion thereof; one or more overhangs complementary to one or more target polynucleotide overhangs; one or more probe binding sites (e.g., for attachment to a sequencing platform, such as a flow cell for massive parallel sequencing, such as flow cells as developed by Illumina, Inc.); one or more random or near-random sequences (e.g., one or more nucleotides selected at random from a set of two or more different nucleotides at one or more positions, with each of the different nucleotides selected at one or more positions represented in a pool of adaptors comprising the random sequence); and any combination thereof. Where multiple ligation products are generated in parallel from multiple single-stranded target sample polynucleotides, a portion of the at least one additional segment of the second single-stranded adaptor may have a nucleic acid sequence identical to that of other ligation products generated.

In some embodiments, the first single-stranded adaptor and/or the second single-stranded adaptor comprises an amplification primer binding sequence, or a portion thereof, and the method further comprises generating a plurality of amplification products. Amplifying a ligation product or a segment of a ligation product comprising a single-stranded target sample polynucleotide ligated to a first single-stranded adaptor and to a second single-stranded adaptor can comprise primer extension of a first primer that specifically hybridizes to a portion of the first single-stranded adaptor, the second single-stranded adaptor, the first extension sequence, the second extension sequence, or complements thereof. Where sequencing analysis of the ligation product is desired, use of an amplification primer comprising a first sequencing adaptor can produce amplification products in which the nucleotide sequence of the first sequencing adaptor is appended to one end of the nucleotide sequence of a ligation product. In some embodiments, the first single-stranded adaptor may itself comprise the first sequencing adaptor. In some embodiments, the first extension sequence of a single-stranded sample polynucleotide may comprise the first sequencing adaptor. The first sequencing adaptor can be used, for example, for binding by a sequencing primer or for attaching the amplification product to a flow cell for next generation sequencing.

A first primer for nucleic acid amplification can be of any suitable length, such as at least 5, 6, 7, 8, 9, 10, 15, 20, 25, 30, 35, 40, 45, 50, 55, 60, 65, 70, 75, 80, 90, or 100 nucleotides or more than 100 nucleotides, any portion or all of which may be complementary to the corresponding target sequence (e.g. about 5, 10, 15, 20, 25, 30, 35, 40, 45, or 50 nucleotides or more than 50 nucleotides). The length of a first primer for nucleic acid amplification can be within a range of 5 to 100 nucleotides, 10 to 85 nucleotides, 15 to 70 nucleotides, or 20 to 60 nucleotides, any portion or all of which may be complementary to the corresponding target sequence (e.g. about 5, 10, 15, 20, 25, 30, 35, 40, 45, or 50 nucleotides or more than 50 nucleotides). A first primer may comprise additional sequence elements including but not limited to a segment comprising one or more amplification primer annealing sequences or complements thereof; one or more sequencing primer annealing sequences or complements thereof, one or more barcode sequences; one or more common sequences shared among multiple different primers; one or more restriction enzyme recognition sites; one or more probe binding sites or sequencing adaptors (e.g. for attachment to a sequencing platform, such as a flow cell for massive parallel sequencing); one or more random or near-random sequences (e.g. one or more nucleotides selected at random from a set of two or more different nucleotides at one or more positions); and combinations thereof.

In some embodiments, the ligation product, a segment of the ligation product, or amplification products thereof, is amplified using a second primer that specifically hybridizes to an extension product of the first primer via sequence complementarity. Where appending a second sequencing adaptor to a ligation product is desired, a second primer comprising a second sequencing adaptor can be used for amplification. The first and second sequencing adaptor may be the same or different. In some embodiments, the second primer comprises at a 5' end a second sequencing adaptor lacking sequence complementarity to an extension product of the first primer. Use of an amplification primer comprising a second sequencing adaptor can produce amplification products from extension products of the first primer in which the nucleotide sequence of an second sequencing adaptor is appended to one end of the sequence of a ligation product, for example at the 3' end of the ligation product if the sequencing adaptor of the first primer is appended at the 5' end of the ligation product. In some embodiments, the sequence of the additional sequencing adaptor is appended at the 5' end of the ligation product if the sequencing adaptor of the first primer is appended at the 3' end of the ligation product. In some embodiments, the second single-stranded adaptor may itself comprise the sequencing adaptor. In some embodiments, the second extension sequence of the single-stranded sample polynucleotide comprises the sequencing adaptor.

A second primer for nucleic acid amplification can be of any suitable length, such as at least 5, 6, 7, 8, 9, 10, 15, 20, 25, 30, 35, 40, 45, 50, 55, 60, 65, 70, 75, 80, 90, or 100 nucleotides, any portion or all of which may be complementary to the corresponding target sequence (e.g. about 5, 10, 15, 20, 25, 30, 35, 40, 45, or 50 nucleotides or more than 50 nucleotides). The length of a second primer for nucleic acid amplification can be within a range of 5 to 100 nucleotides, 10 to 85 nucleotides, 15 to 70 nucleotides, or 20 to 60 nucleotides, any portion or all of which may be complementary to the corresponding target sequence (e.g. about 5, 10, 15, 20, 25, 30, 35, 40, 45, or 50 nucleotides or more than 50 nucleotides). A second primer may comprise additional sequence elements including but not limited to a segment comprising one or more amplification primer annealing sequences or complements thereof, one or more sequencing primer annealing sequences or complements thereof, one or more barcode sequences; one or more common sequences shared among multiple different primers; one or more restriction enzyme recognition sites; one or more probe binding sites or sequencing adaptors (e.g. for attachment to a sequencing platform, such as a flow cell for massive parallel sequencing); one or more random or near-random sequences (e.g. one or more nucleotides selected at random from a set of two or more different nucleotides at one or more positions); and combinations thereof.

In general, the term "amplification" refers to a process by which one or more copies are made of a target polynucleotide or a portion thereof. The resulting copies can be referred to as "amplification product(s)." In some embodiments, amplification comprises at least one primer extension reaction. A variety of methods of amplifying polynucleotides (e.g. DNA and/or RNA) are available. Amplification may be linear, exponential, or involve both linear and exponential phases in a multi-phase amplification process. Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. Nos. 5,527,670, 6,033,850, 5,939,291, and 6,333,157), and application of an electromagnetic field in combination with primers bound to a magnetically-responsive material (e.g. U.S. Pat. No. 5,545,540).

One example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method. Other amplification methods include rolling circle amplification (RCA); helicase dependent amplification (HDA); and loop-mediated isothermal amplification (LAMP). In some cases, isothermal amplification utilizes transcription by an RNA polymerase from a promoter sequence, such as may be incorporated into an oligonucleotide primer. Transcription-based amplification methods include nucleic acid sequence based amplification, also referred to as NASBA; methods which rely on the use of an RNA replicase to amplify the probe molecule itself, commonly referred to as QP replicase; self-sustained sequence replication; and methods for generating additional transcription templates. Further methods of isothermal nucleic acid amplification include the use of primers containing non-canonical nucleotides (e.g. uracil or RNA nucleotides) in combination with an enzyme that cleaves nucleic acids at the non-canonical nucleotides (e.g. DNA glycosylase or RNaseH) to expose binding sites for additional primers. Isothermal amplification processes can be linear or exponential.

In an aspect, the present disclosure provides a method of preparing a plurality of ligation products comprising single-stranded target sample polynucleotides for sequencing without performing solid-phase based enrichment of the single-stranded target sample polynucleotides, wherein a single-stranded target sample polynucleotide comprises a target polynucleotide joined to a first extension sequence at a 5' end of the target polynucleotide and to a second extension sequence at a 3' end of the target polynucleotide. In some embodiments, the method comprises (a) providing a plurality of ligation products, wherein an individual ligation product of the plurality is generated by: (i) mixing a single-stranded target sample polynucleotide, a first single-stranded adaptor, a second single-stranded adaptor, a first bridging probe, and a second bridging probe to form a polynucleotide complex, the polynucleotide complex includes (a) a 5' end of the first bridging probe specifically hybridized to a 3' end of the first single-stranded adaptor via sequence complementarity, and a 5' end of the single-stranded target sample polynucleotide specifically hybridized to a 3' end of the first bridging probe via sequence complementarity, and (b) a 5' end of the second bridging probe specifically hybridized to a 3' end of the single-stranded target sample polynucleotide via sequence complementarity, and a 5' end of the second single-stranded adaptor specifically hybridized to a 3' end of the second bridging probe via sequence complementarity, (ii) ligating (a) the 3' end of the first single-stranded adaptor to the 5' end of the single-stranded target sample polynucleotide and (b) the 3' end of the single-stranded target sample polynucleotide to the 5' end of the second single-stranded adaptor, and (iii) degrading or selectively removing the first and second bridging probes, thereby forming the ligation product; and optionally (b) subjecting the plurality of ligation products, or amplification products thereof, to a sequencing reaction. In some embodiments, (i)-(iii) of (a) occurs in a single reaction mixture. In some embodiments, (i)-(iii) of (a) are performed without altering a concentration of the single-stranded target sample polynucleotides in the reaction mixture, for example via solid-phase based enrichment methods.

Ligation products can be subjected to sequencing directly. In some cases, sequencing may be preceded by one or more amplification reactions, as previously described, and the amplification products are subjected to sequencing. In some embodiments, the ligation products and/or amplification products thereof are isolated and/or enriched prior to sequencing. Isolation can be achieved by various suitable purification methods including, but not limited to, affinity purification.

Ligation products, and amplification products thereof, can be subjected to a sequencing reaction to generate sequencing reads. A variety of sequencing methodologies are available, particularly high-throughput sequencing methodologies. Examples include, without limitation, sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300, or more nucleotides in length. In some embodiments, sequencing comprises a sequencing by synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the a and p phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence.

In related sequencing processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. For example, immobilization of the complex can be via a linkage between the polymerase or the primer and the substrate surface. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex, allowing identification of the incorporated nucleotide. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. For example, the Illumina Genome Analyzer System is based on technology described in WO 98/44151, wherein DNA molecules are bound to a sequencing platform (flow cell) via an anchor probe binding site (otherwise referred to as a flow cell binding site) and amplified in situ on a glass slide. A solid surface on which DNA molecules are amplified typically comprise a plurality of first and second bound oligonucleotides, the first complementary to a sequence near or at one end of a target polynucleotide and the second complementary to a sequence near or at the other end of a target polynucleotide. This arrangement permits bridge amplification. The DNA molecules are then annealed to a sequencing primer and sequenced in parallel base-by-base using a reversible terminator approach. Hybridization of a sequencing primer may be preceded by cleavage of one strand of a double-stranded bridge polynucleotide at a cleavage site in one of the bound oligonucleotides anchoring the bridge, thus leaving one single strand not bound to the solid substrate that may be removed by denaturing, and the other strand bound and available for hybridization to a sequencing primer.

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a $\beta,\gamma$, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated.

In some embodiments, the nucleic acids in the sample can be sequenced by ligation. This method typically uses a DNA ligase enzyme to identify the target sequence, for example, as used in the polony method and in the SOLiD technology (Applied Biosystems, now Invitrogen). In general, a pool of all possible oligonucleotides of a fixed length is provided, labeled according to the sequenced position. Oligonucleotides are annealed and ligated; the preferential ligation by DNA ligase for matching sequences results in a signal corresponding to the complementary sequence at that position.

Sequencing reads produced by sequencing amplification products generated by the methods herein using various suitable sequencing technologies can then be used for sequence variant detection. In some embodiments, identifying a genuine sequence variant (also referred to as "calling" or "making a call") comprises optimally aligning one or more sequencing reads with a reference sequence to identify differences between the two. In general, alignment involves placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome consists only of regions containing target polynucleotides, such as from a reference genome or from a consensus generated from sequencing reads under analysis. In some embodiments, a reference sequence comprises or consists of sequences of polynucleotides of one or more organisms, such as sequences from one or more bacteria, archaea, viruses, protists, fungi, mammal or other organism. In some embodiments, the reference sequence consists of only a portion of a reference genome, such as regions corresponding to one or more target sequences under analysis (e.g. one or more genes, or portions thereof). For example, for detection of a pathogen (such as in the case of contamination detection), the reference genome is the entire genome of the pathogen (e.g. HIV, HPV, or a harmful bacterial strain, e.g. *E. coli*), or a portion thereof useful in identification, such as of a particular strain or serotype. For further example, for detection of a sequence variant associated with a disease or diseased state, including but not limited to cancer, the reference genome is the entire genome of the subject (e.g. mammal, e.g., human), or a portion thereof useful in identifying a mutated gene. In some embodiments, sequencing reads are aligned to multiple different reference sequences.

In a typical alignment, a base in a sequencing read alongside a non-matching base in the reference indicates that a substitution mutation has occurred at that point. Similarly, where one sequence includes a gap alongside a base in the other sequence, an insertion or deletion mutation (an "indel") is inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments. In some embodiments, scoring an alignment involves setting values for the probabilities of substitutions and indels. When individual bases are aligned, a match or mismatch contributes to the alignment score by a substitution probability, which could be, for example, 1 for a match and 0.33 for a mismatch. An indel deducts from an alignment score by a gap penalty, which could be, for example, −1. Gap penalties and substitution probabilities can be based on empirical knowledge or a priori assumptions about how sequences mutate. Their values affect the resulting alignment. Examples of algorithms for performing alignments include, without limitation, the Smith-Waterman (SW) algorithm, the Needleman-Wunsch (NW) algorithm, algorithms based on the Burrows-Wheeler Transform (BWT), and hash function aligners such as Novoalign (Novocraft Technologies; available at www.novocraft.com), ELAND (Illumina, San Diego, Calif.), SOAP (available at soap.genomics.org.cn), and Maq (available at maq.sourceforge.net). One exemplary alignment program, which implements a BWT approach, is Burrows-Wheeler Aligner (BWA) available from the SourceForge web site maintained by Geeknet (Fairfax, Va.). BWT typically occupies 2 bits of memory per nucleotide, making it possible to index nucleotide sequences as long as 4G base pairs with a typical desktop or laptop computer. The pre-processing includes the construction of BWT (i.e., indexing the reference) and the supporting auxiliary data structures. BWA includes two different algorithms, both based on BWT. Alignment by BWA can proceed using the algorithm bwa-short, designed for short queries up to about 200 by with low error rate (<3%) (Li H. and Durbin R. Bioinformatics, 25:1754-60 (2009)). The second algorithm, BWA-SW, is designed for long reads with more errors (Li H. and Durbin R. (2010). Fast and accurate long-read alignment with Burrows-Wheeler Transform. Bioinformatics, Epub.). The bwa-sw aligner is sometimes referred to as "bwa-long", "bwa long algorithm", or similar. An alignment program that implements a version of the Smith-Waterman algorithm is MUMmer, available from the SourceForge web site maintained by Geeknet (Fairfax, Va.). MUMmer is a system for rapidly aligning entire genomes, whether in complete or draft form (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can also align incomplete genomes; it can easily handle the 100s or 1000s of contigs from a shotgun sequencing project, and will align them to another set of contigs or a genome using the NUCmer program included with the system. Other non-limiting examples of alignment programs include: BLAT from Kent Informatics (Santa Cruz, Calif.) (Kent, W. J., Genome Research 4: 656-664 (2002)); SOAP2, from Beijing Genomics Institute (Beijing, Conn.) or BGI Americas Corporation (Cambridge, Mass.); Bowtie (Langmead, et al., Genome Biology, 10:R25 (2009)); Efficient Large-Scale Alignment of Nucleotide Databases (ELAND) or the ELANDv2 component of the Consensus Assessment of Sequence and Variation (CASAVA) software (Illumina, San Diego, Calif); RTG Investigator from Real Time Genomics, Inc. (San Francisco, Calif); Novoalign from Novocraft (Selangor, Malaysia); Exonerate, European Bioinformatics Institute (Hinxton, UK) (Slater, G., and Birney, E., BMC Bioinformatics 6:31 (2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985)).

In another aspect, the disclosure provides a reaction mixture for forming a ligation product comprising a single-stranded sample polynucleotide in accordance with methods disclosed herein. In some embodiments, the single-stranded sample polynucleotide comprises a target polynucleotide joined to a first extension sequence at a 5' end of the target polynucleotide and to a second extension sequence at a 3' end of the target polynucleotide. A reaction mixture can comprise one or more of the various components as described herein with respect to any of the various aspects and methods of the present disclosure. In some embodiments, the reaction mixture comprises (a) a mixture of the single-stranded sample polynucleotide, a first single-stranded adaptor, a second single-stranded adaptor, a first bridging probe, and a second bridging probe, wherein (i) a 5' end of the first bridging probe specifically hybridizes to a 3' end of the first single-stranded adaptor via sequence complementarity, and a 3' end of the first bridging probe specifically hybridizes to a 5' end of the single-stranded sample polynucleotide via sequence complementarity, and (ii) a 5' end of the second bridging probe specifically hybridizes to a 3' end of the single-stranded sample polynucleotide via sequence complementarity, and a 3' end of the second bridging probe specifically hybridizes to a 5' end of the second single-stranded adaptor via sequence complementarity; and (b) a ligase to effect (i) ligation of the 3' end of the first single-stranded adaptor to the 5' end of the single-stranded sample polynucleotide and (ii) ligation of the 3' end of the single-stranded sample polynucleotide to the 5' end of the second single-stranded adaptor. Examples of the single-stranded sample polynucleotides, first single-stranded adaptors, second single-stranded adaptors, and bridging probe are described herein, such as with regard to any of the various aspects of the disclosure.

In some embodiments, the single-stranded sample polynucleotide, first single-stranded adaptor, the second single-stranded adaptor, and the bridging probes in a reaction mixture form a polynucleotide complex. The formation of a polynucleotide complex, as discussed elsewhere herein, can depend on the length (in nucleotides) of the hybridized portions, the degree of sequence complementarity between the hybridized portions, and the temperature at which the mixing is conducted. The length of the hybridized portions of a polynucleotide complex can be any suitable length, as previously described.

In some embodiments, the first bridging probe hybridizes to at least a portion of the first extension sequence at the 5' end of the single-stranded sample polynucleotide. In some embodiments, the first bridging probe hybridizes to the entire first extension sequence and at least a portion of the target polynucleotide at the 5' end of the single-stranded sample polynucleotide. In some embodiments, a segment of the 5' end of the target polynucleotide does not specifically hybridize to the first bridging probe, for example due to lack of sequence complementarity, and the segment forms a first single-stranded loop in the polynucleotide complex. In some embodiments, the first single-stranded loop is excised prior to ligating the first single-stranded adaptor to the single-stranded sample polynucleotide. In some embodiments, the first single-stranded loop is excised concurrently with ligating the first single-stranded adaptor to the single-stranded sample polynucleotide. The first single-stranded loop can be excised, for example, by an enzyme with nuclease activity. In some embodiments, the loop is not excised. In some embodiments, a segment of the first bridging probe does not specifically hybridize to the 5' end of the target polynucleotide, for example due to lack of sequence complementarity, and the segment forms a first single-stranded loop (e.g., the loop is formed in the first bridging probe).

In some embodiments, the second bridging probe hybridizes to at least a portion of the second extension sequence at the 3' end of the single-stranded sample polynucleotide. In some embodiments, the second bridging probe hybridizes to the entire second extension sequence and at least a portion of the target polynucleotide at the 3' end of the single-stranded sample polynucleotide. In some embodiments, a segment of the 3' end of the target polynucleotide does not specifically hybridize to the second bridging probe, for example due to lack of sequence complementarity, and the segment forms a second single-stranded loop in the polynucleotide complex. This loop can similarly be excised, for example by an enzyme with nuclease activity, prior to or concurrent with ligating the single-stranded sample polynucleotide to the second single-stranded adaptor. However, in some cases, this loop is not excised. However, in some cases, this loop is not excised. In some embodiments, a segment of the second bridging probe does not specifically hybridize to the 3' end of the target polynucleotide, for example due to lack of sequence complementarity, and the segment forms a second single-stranded loop in the polynucleotide complex (e.g., the loop is formed in the second bridging probe).

In some embodiments, as previously described, a first single-stranded loop and a second single-stranded loop are both formed in the polynucleotide complex.

In some embodiments, the single-stranded sample polynucleotide is a cell-free polynucleotide, including but not limited to a cell-free DNA or RNA (cfDNA or cfRNA). In some embodiments, the sample polynucleotide is a cell-free DNA which comprises a sequence variant. In some embodiments, the sequence variant comprises at least one of a single nucleotide polymorphism, a single nucleotide variant, an insertion, a deletion, a duplication, an inversion, a translocation, a copy number variation, a gene fusion, and a mutation indicative of methylation. In some embodiments, the target polynucleotide comprises a linear concatemer having at least one copy of a cell-free DNA sequence, or a complement thereof (e.g., at least 1, 2, 3, 4, 5, 6, 7, 8, 9, or 10 copies or more). In some embodiments, the target polynucleotide comprises genomic DNA or a fragment thereof. In some embodiments, the target polynucleotide comprises a linear concenter having at least one copy of a fragment of genomic DNA or a complement thereof (e.g., at least 1, 2, 3, 4, 5, 6, 7, 8, 9, or 10 copies or more).

In some embodiments, a bridging probe can be removed from a reaction mixture by degradation or selective removal as described above. Removing a bridging probe may occur concurrent with or following the formation of a ligation product. In some embodiments, a single-stranded sample polynucleotide, a first single-stranded adaptor, and a second single-stranded adaptor comprise DNA while the bridging probes comprise RNA. In some embodiments, a reaction mixture comprises an RNA endonuclease that can selectively degrade the bridging probes comprising RNA. In some embodiments, a reaction mixture comprises an RNA exonuclease that can selectively degrade the bridging probes comprising RNA. In some embodiments, a single-stranded sample polynucleotide, first single-stranded adaptor, and second single-stranded adaptor comprise RNA while the bridging probes comprise DNA. In some embodiments, a reaction mixture comprises a DNA endonuclease that can selectively degrade the DNA bridging probe. In some embodiments, a bridging probe comprises deoxyuridines. In some embodiments, a bridging probe comprises at least 1 deoxyuridine (e.g. at least 2, 5, 10, 20, 30 deoxyuridines or more than 30 deoxyuridines). In some embodiments, a bridging probe comprising deoxyuridines comprises at least 1% deoxyuridines (e.g. at least 2%, 3%, 4%, 5%, 6%, 7%, 8%, 9%, 10% deoxyuridines or more than 10% deoxyuridines). In some embodiments, a bridging probe comprises between 5% and 50% deoxyuridines. In some embodiments, a reaction mixture comprises a uracil DNA-glycosylase that can degrade a bridging probe comprising one or more deoxyuridines. In some embodiments, the bridging probe comprises a tag, for example biotin. In some embodiments, a bridging probe comprises a tag that selectively binds to a binding element. The bridging probe can be removed by a binding element that selectively binds to the tag. In some embodiments, the tag is biotin. Where selectively removing a bridging probe comprising a biotin tag is desired, a binding element comprising avidin, modified avidin, or streptavidin can be used.

In some embodiments, the bridging probe is degraded chemically. Chemical degradation can be effected by chemical agents that degrade RNA such as sodium hydroxide; or chemical agents that degrade DNA such as natural antibiotics (e.g. bleomycin, neocarzinostatin) or synthetic reagents (e.g. methidiumpropyl-EDTA iron(II) complexes).

In some embodiments, a reaction mixture of the present disclosure is contained in a container. Each component may be packaged into different containers or where cross-reactivity and shelf-life permit, combinations of components can be provided in containers. Non-limiting examples of containers include a well, a plate, a tube, a chamber, a flow cell, and a chip.

In another aspect, the disclosure provides kits for performing methods in accordance with the methods of the disclosure. Kits can comprise one or more elements disclosed herein in relation to any of the various aspects, in any combination. In some embodiments, the kit is used for generating a plurality of ligation products comprising a single-stranded sample polynucleotide joined to a first single-stranded adaptor and a second-single-stranded adaptor. A single-stranded sample polynucleotide, as previously described herein, can comprise a target polynucleotide joined to a first extension sequence at the 5' end of the target polynucleotide and to a second extension sequence at the 3' end of the target polynucleotide. In some embodiments, a kit of the disclosure comprises a plurality of first bridging probes, a plurality of second bridging probes, a plurality of first single-stranded adaptors, a plurality of second single-stranded adaptors, and instructions for using the plurality of first and second bridging probes for generating a plurality of ligation products. In some embodiments, a given first bridging probe comprises (i) a 5' end exhibiting sequence complementarity to a 3' end of a given first single-stranded adaptor, and (ii) a 3' end exhibiting sequence complementarity to a 5' end of a single-stranded sample polynucleotide. In some embodiments, a given second bridging probe comprises (i) a 5' end exhibiting sequence complementarity to a 3' end of the single-stranded sample polynucleotide, and (ii) a 3' end exhibiting sequence complementarity to a 5' end of a given second single-stranded adaptor. In some embodiments, the first bridging probes, the second bridging probes, or both the first and second bridging probes of a kit comprises deoxynucleotides, ribonucleotides, deoxyuridines, or any combination thereof.

In some embodiments, the kit further comprises a uracil DNA-glycosylase, an endonuclease (e.g., a DNA endonuclease, an RNA endonuclease), an exonuclease (e.g., a DNA exonuclease, an RNA exonuclease), a polymerase, and/or a ligase for practicing the methods of the various embodiments disclosed herein. In some embodiments, a kit comprises one or more bridging probes (e.g. DNA probes and/or RNA probes); one or more bridging probes labeled with tags (e.g. bridging probes labeled with biotin); one or more binding elements that selectively binds a tag (e.g. binding elements comprising avidin or modified avidin or streptavidin); one or more bridging probes comprising at least one deoxyuridine; one or more uracil DNA-glycosylases; one or more first single-stranded adaptors; one or more second single-stranded adaptors; one or more ligases and associated buffers and reagents; one or more polymerases and associated buffers and reagents, including for example dNTPs; one or more endonucleases (e.g. DNA endonuclease and/or RNA endonuclease); one or more exonucleases (e.g., DNA exonuclease and/or RNA exonuclease); one or more reagents for chemically degrading a bridging probe, e.g., sodium hydroxide; one or more amplification primers, e.g., for generating amplification product; and combinations thereof provided in one or more containers.

In one aspect, the present disclosure provides a polynucleotide complex useful for forming a ligation product. The complex can be any of the complexes formed by a method described herein, such as with regard to any of the various aspects of the disclosure. In some embodiments, a polynucleotide complex comprises a single-stranded target sample polynucleotide, a first single-stranded adaptor, a second-single stranded adaptor, a first bridging probe, and a second bridging probe, wherein the single-stranded target sample polynucleotide comprises a target polynucleotide joined to a first extension sequence at the 5' end of the target polynucleotide and to a second extension sequence at the 3' end of the target polynucleotide. In some embodiments, (i) a 5' end of the first bridging probe specifically hybridizes to a 3' end of the first single-stranded adaptor via sequence complementarity, and a 5' end of the single-stranded sample polynucleotide specifically hybridizes to a 3' end of the first bridging probe via sequence complementarity, and (ii) a 5' end of the second bridging probe specifically hybridizes to a 3' end of the single-stranded target sample polynucleotide via sequence complementarity, and a 5' end of the second single-stranded adaptor specifically hybridizes to a 3' end of the second bridging probe via sequence complementarity. In some embodiments, the first bridging probe, the second bridging probe, or both the first and second bridging probes comprises deoxynucleotides, ribonucleotides, deoxyuridines, or any combination thereof. In some embodiments, at least one of the first bridging probe and the second bridging probe comprises at least five deoxyuridines.

In some embodiments, the single-stranded target sample polynucleotide comprises a cell-free polynucleotide, including but not limited to a cell-free DNA or RNA (cfDNA or cfRNA). In some embodiments, the target polynucleotide comprises a cell-free polynucleotide. In some embodiments, the single-stranded target sample polynucleotide comprises a fragment of genomic DNA. In some embodiments, the target polynucleotide comprises a fragment of genomic DNA. In some embodiments, the single-stranded target sample polynucleotide comprises a sequence resulting from a chromosomal rearrangement. In some embodiments, the chromosomal rearrangement is at least one of a deletion, duplication, inversion, and translocation. In some embodiments, the target polynucleotide comprises a sequence resulting from a chromosomal rearrangement. In some embodiments, the chromosomal rearrangement is at least one of a deletion, duplication, inversion, and translocation.

Various embodiments of the aspects described herein, including the methods, reaction mixtures, kits, and polynucleotide complexes, comprise at least one bridging probe. A bridging probe can be of any suitable length. In some embodiments, a bridging probe is at least 30 nucleotides (e.g. at least 50, 60, 70, 80, 90, 100, 150, 200, 250, 300, 350, 400, 450, or 500 nucleotides or more than 500 nucleotides) in length. In some embodiments, a bridging probe is more than 100 nucleotides in length. In some embodiments, a bridging probe is between 30 and 500 nucleotides (e.g. between 40 and 400 nucleotides, between 50 and 300 nucleotides, or between 75 and 200 nucleotides) in length. A bridging probe can comprise nucleotides such as deoxyribonucleotides, ribonucleotides, and combinations thereof. In some embodiments, a bridging probe comprises one or more modified nucleotides, such as methylated nucleotides and nucleotide analogs. In some embodiments, a bridging probe comprises aminoallyl, biotin, and/or 2' fluoro modifications. In some embodiments, a bridging probe comprises modified nucleotides, examples of which include but are not limited to bisphosphates, a series of monophosphates and ARCA, CAP and mCAP. A bridging probe may comprise aminoallyl modified nucleotides. Aminoallyl modifications can allow amine reactive moieties, such as a fluorescent dye, biotin, hapten or protein, to be conjugated to the bridging probe. Aminoallyl nucleotides can also be used for indirect DNA labeling in PCR, nick translation, primer extensions and cDNA synthesis. In some embodiments, a bridging probe comprises 1 modified nucleotide. In some embodiments, a bridging probe comprises at least 1 modified nucleotide (e.g. at least 2, 5, 10, 15, 20, 30, 40, 50 modified nucleotides or more than 50 modified nucleotides). In some embodiments, a bridging probe comprises at least 1% modified nucleotides (e.g. at least 2%, 3%, 4%, 5%, 6%, 7%, 8%, 9%, 10% modified nucleotides or more than 10% modified nucleotides). In some embodiments, a bridging probe comprises between 10% and 100% modified nucleotides (e.g. between 20% and 90% modified nucleotides, between 30% and 80% modified nucleotides, or between 40% and 70% modified nucleotides). In some embodiments, a bridging probe comprises deoxyuridines. In some embodiments, a bridging probe comprises at least 1 deoxyuridine (e.g. at least 2, 5, 10, 20, 30 deoxyuridines or more than 30 deoxyuridines). In some embodiments, a bridging probe comprises at least 1% deoxyuridines (e.g. at least 2%, 3%, 4%, 5%, 6%, 7%, 8%, 9%, 10% deoxyuridines or more than 10% deoxyuridines). In some embodiments, a bridging probe comprises between 5% and 50% deoxyuridines.

Certain embodiments of the various aspects of the present disclosure comprise degrading a bridging probe. Degrading the bridging probe can comprise degrading the bridging probe enzymatically. In some embodiments, a bridging probe comprising deoxyuridines is degraded by a uracil DNA-glycosylase. In some embodiments, a bridging probe is degraded by a nuclease, an endonuclease, an exonuclease, and/or a ribonuclease, including endoribonucleases and exoribonucleases. DNA endonucleases can include type I endonucleases and type II endonucleases. Non-limiting examples of enzymes that can degrade polynucleotides and bridging probes include DNase I, micrococcal nuclease, nuclease Si, mung bean nuclease, exonuclease II, exonuclease III, exonuclease IV, exonuclease V, exonuclease VI, exonuclease VII, exonuclease VIII, RNase A, RNase I, RNase III, RNase T1, phosphodiesterase I, phosphodiesterase II, and RNase H.

In some embodiments, the bridging probe is degraded chemically. Chemical degradation can be effected by chemical agents that degrade RNA such as sodium hydroxide; or chemical agents that degrade DNA such as natural antibiotics (e.g. bleomycin, neocarzinostatin) or synthetic reagents (e.g. methidiumpropyl-EDTA iron(II) complexes).

Certain embodiments of the various aspects of the present disclosure comprise a bridging probe comprising a tag. A tag can comprise a molecular structure that, once attached to a bridging probe, provides a distinct characteristic that is not inherent to the bridging probe lacking the tag, such as selective binding to a binding element. A bridging probe comprising a tag can be selectively removed by a binding element that selectively binds the tag. In some embodiments, a bridging probe is modified at an end or a terminus of the probe, such as at a 3' end or a 5' end. In some embodiments, a bridging probe is modified at any nucleotide along the length of the bridging probe. In some embodiments, a bridging probe is modified at one nucleotide. In some embodiments, a bridging probe is modified at more than one nucleotide. A tag can be used for the selective removal of the bridging probe by using a binding element that selectively binds the tag. Prior to selective removal of the bridging probe, a tag can also be used to isolate the complex of polynucleotides such that unhybridized and/or unligated polynucleotides can be removed from the sample volume prior to further analysis and amplification steps. A bridging probe may comprise a hapten, biotin or other protein tag. In some embodiments, a tag is a chemical or small molecule tag. In some embodiments of the various aspects of the disclosure, a bridging probe comprises a biotin tag. A biotin tag can bind a binding element comprising an avidin, modified avidin, or streptavidin protein. An avidin can be tetrameric or dimeric. An avidin protein may be in a deglycosylated form with modified arginines, such as neutravidin, and can exhibit a more neutral isoelectric point relative to native avidin. Other examples of deglycosylated, neutral forms of avidin include Extravidin (Sigma-Aldrich), NeutrAvidin (Thermo Scientific), NeutrAvidin (Invitrogen), and NeutraLite (Belovo). In some embodiments, a bridging probe comprises a biotin tag at a 5' end. In some embodiments, a bridging probe comprises more than one biotin tag at a 5' end. In some embodiments, a bridging probe comprises a biotin tag at a 3' end. In some embodiments, a bridging probe comprises more than one biotin tag at a 3' end. In some embodiments, a bridging probe comprises a biotin tag at both a 3' end and a 5' end. In some embodiments, a bridging probe comprises at least one biotin tag along the length of the bridging probe. In some embodiments, the binding partner comprising avidin, modified avidin, or streptavidin is attached to a solid support, such as a particle or bead. In some embodiments, a particle or bead attached to a binding partner comprising avidin, modified avidin, or streptavidin is magnetic. In some embodiments, the magnetic particles and/or beads comprising a binding partner is used to selectively remove a bridging probe by binding the tag to the binding partner and a magnet is used to remove the beads. In some embodiments, a plurality of particles or beads attached to a binding partner comprising avidin, modified avidin, or streptavidin are packed into a column and column chromatography is used to remove the bridging probe. In some embodiments, a bridging probe comprises a digoxigenin tag. A bridging probe can comprise at least one digoxigenin tag along the length of the bridging probe. A digoxigenin tag can bind a binding element comprising an anti-digoxigenin antibody. In some embodiments, a binding element comprising an anti-digoxigenin antibody is attached to a solid support. In some embodiments, a bridging probe comprises a dinitrophenol (DNP) tag. A bridging probe can comprise at least one dinitrophenol tag along the length of bridging probe. A DNP tag can bind a binding element comprising an anti-DNP antibody. In some embodiments, a binding element comprising an anti-DNP antibody is attached to a solid support. In some embodiments, a bridging probe comprises a fluorescein tag. A bridging probe can comprise at least one fluorescein tag along the length of the bridging probe. A fluorescein tag can bind a binding element comprising an anti-fluorescein antibody. In some embodiments, a binding element comprising an anti-fluorescein antibody is attached to a solid support. Non-limiting examples of pairs of binding partners, one of which may be used as a tag and the other of which may be used as the binding element for removing probes comprising the tag, include antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine); biotin/avidin (or biotin/streptavidin); calmodulin binding protein (CBP)/calmodulin; hormone/hormone receptor; lectin/carbohydrate; peptide/cell membrane receptor; protein A/antibody; hapten/antihapten; enzyme/cofactor; and enzyme/substrate.

The coupling of a tag to a bridging probe can be performed using a variety of methods. In some embodiments, tags are coupled to a bridging probe by direct attachment or by attachment through one or more linkers (e.g. linker molecules) and the formation of a covalent bond. In some embodiments, tags are coupled to a bridging probe by an electrostatic interaction that does not involve a covalent bond. In some embodiments, the tags are chemically attached during in-vitro amplification (e.g. by PCR) using labeled primers. Amplification can comprise a number of different molecular replication or amplification approaches, including but not limited to polymerase chain reaction (PCR), asymmetric PCR, multiplex PCR, nested PCR, hot-start PCR, touchdown PCR, RT-PCR, and methylation-specific PCR. Amplification can be isothermal, including, but not limited to, loop-mediated isothermal amplification (LAMP), strand displacement amplification (SDA), heliembodiment-dependent amplification (HDA), and nicking enzyme amplification reaction (NEAR). In some embodiments, the labels are attached to modified nucleotides which are used to assemble the bridging probe. Hapten labeled nucleotides, such as digoxigenin labeled nucleotides, and biotin labeled nucleotides can be incorporated into a bridging probe with a variety of DNA or RNA polymerases including SP6, T7, AMV, M-MuLV, DNA Polymerase 1, Taq, Pfu, Klenow fragment, and TdT. Biotin labeled nucleotides can be incorporated into a bridging probe with a variety of DNA or RNA polymerases including SP6, T7, AMV, M-MuLV, DNA Polymerase 1, Taq, Pfu, Klenow fragment, and TdT.

In some embodiments of the various aspects herein, a single-stranded sample polynucleotide or a single-stranded target sample polynucleotide comprises a target polynucleotide joined to extension sequences at the 5' and 3' end of the target polynucleotide. In some embodiments, the target polynucleotide comprises a cell-free polynucleotide, including but not limited to a cell-free DNA or RNA (cfDNA or cfRNA). Any cell-free polynucleotide can be used by embodiments of the present disclosure. Cell-free polynucleotides can be obtained from a subject, such as any animal or living organism. Non-limiting examples of subjects are mammals, such as humans, non-human primates, rodents such as mice and rats, dogs, cats, pigs, sheep, rabbits and others. In some embodiments, a subject is healthy, and cell-free polynucleotides obtained from the subject may not comprise a sequence variant associated with a disease or disorder. In some embodiments, a subject is suspected of having a disease or disorder, and cell-free polynucleotides obtained from the subject may comprise a sequence variant associated with the disease or disorder. In some embodiments, a subject is pregnant, and cell-free polynucleotides obtained from the subject comprise fetal polynucleotides.

In some embodiments, a cell-free polynucleotide is a circulating tumor DNA or RNA (ctDNA or ctRNA). In some embodiments, a cell-free polynucleotide comprises fetal DNA or RNA. In some embodiments, cell-free polynucleotides are polynucleotides originating from a cell but not directly obtained from a cellular source (e.g. by an extraction step comprising cell lysis). Non-limiting examples of sources from which cell-free polynucleotides may originate are normal cells and tissue, abnormal cells and tissue (e.g. cancerous cells or tissue), fetal cells and tissue, and pathogens. A cell-free polynucleotide present in a non-cellular source can result from cell death (e.g. apoptosis or necrosis) or cell shedding. Sequence analysis of cell-free polynucleotides can be used to characterize the cell or population of cells from which the cell-free DNA is derived, such as tumor cells (e.g. in cancer detection), fetal cells (e.g. in prenatal diagnostics), cells from transplanted tissue (e.g. in early detection of transplant failure), or a pathogen (e.g. bacteria or virus). In some embodiments, is the single-stranded sample polynucleotide comprises a fragment of genomic DNA. In some embodiments, the single-stranded sample polynucleotide comprises a sequence or sequences resulting from a chromosomal rearrangement. In some embodiments, the chromosomal rearrangement is at least one of a deletion, duplication, inversion, and translocation. In some embodiments, the single-stranded sample polynucleotide comprises RNA.

Cell-free polynucleotides can be obtained from various non-cellular sources. Non-limiting examples of non-cellular sources from which cell-free polynucleotides can be obtained are serum, plasma, blood, perspiration, saliva, urine, stool, semen, mucosal excretions, spinal fluid, amniotic fluid, and lymph fluid. Various methods for collecting samples of non-cellular sources from which cell-free polynucleotides can be obtained are available. In some embodiments, samples of non-cellular sources from which cell-free polynucleotides can be obtained are obtained from a subject. In some embodiments, samples are obtained by venipuncture. In some embodiments, samples are obtained by aspiration.

Various methods and commercial kits are available for obtaining cell-free polynucleotides, such as cell-free DNA, from a sample. Examples of methods and kits for extracting and isolating cell-free polynucleotides, including cell-free DNA, are phenol/chloroform extraction, phenol/chloroform/isoamyl alcohol (PCI)-glycogen extraction, NaI (sodium iodide) extraction, guanidine-resin extraction, the QIAmp DNA Blood Midi kit with carrier RNA, the ChargeSwitch serum kit, the ZR serum DNA kit, Qiagen Qubit™ dsDNA HS Assay kit, Agilent™ DNA 1000 kit, TruSeq™ Sequencing Library Preparation, and the Puregene DNA purification system Blood Kit.

Cell-free polynucleotides, including cell-free DNA, can be extracted and isolated from bodily fluids through a partitioning step in which cell-free polynucleotides are separated from cells and other non-soluble components of the bodily fluid. Examples of partitioning techniques are centrifugation and filtration. In some embodiments, cells are not partitioned from cell-free polynucleotides first, but rather lysed. In some embodiments, the genomic DNA of intact cells is partitioned through selective precipitation. Cell-free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments of any of the various aspects disclosed herein, a target polynucleotide of a single-stranded sample polynucleotide or a single-stranded target sample polynucleotide comprises genomic DNA, or a fragment thereof. Genomic DNA can be obtained from a cell sample using various methods and commercial kits available, such as a Qiagen DNeasy Tissue Kit. Genomic DNA can be obtained and purified from a sample using any extraction, isolation, and purification method previously described elsewhere herein. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). For example, nucleic acids can be isolated and purified using solid phase reversible immobilization (SPRI) beads (Agencourt AMPure XP). In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodide, Hoechst stain, SYBR gold, ethidium bromide).

In some embodiments, a target polynucleotide comprises fragmented cell-free DNA or fragmented genomic DNA. Various methods are available for fragmenting polynucleotides, including but not limited to chemical, enzymatic, and mechanical methods such as sonication, shearing, and contacting with restriction enzymes. In some embodiments, cell-free DNA fragments are approximately uniform in length. In some embodiments, cell-free DNA fragments are not approximately uniform in length. In some embodiments, cell-free DNA fragments have an average length from about 50 to about 1000 nucleotides in length. In some embodiments, cell-free DNA fragments have an average length from about 50 to about 500 nucleotides in length. In some embodiments, cell-free DNA fragments have an average length from about 50 to about 250 nucleotides in length. In some embodiments, cell-free DNA fragments have an average length from about 50 to about 200 nucleotides in length. In some embodiments, cell-free DNA fragments have an average length from about 50 to about 100 nucleotides in length. In some embodiments, genomic DNA is fragmented into polynucleotides of shorter lengths. In some embodiments, genomic DNA fragments are approximately uniform in length. In some embodiments, genomic DNA fragments are not approximately uniform in length. In some embodiments, genomic DNA fragments have an average length from about 50 to about 100 nucleotides in length. In some embodiments, genomic DNA fragments have an average length from about 50 and 250 nucleotides in length. In some embodiments, genomic DNA fragments have an average length from about 50 and 500 nucleotides in length. In some embodiments, genomic DNA fragments have an average length from about 50 and 750 nucleotides in length. In some embodiments, genomic DNA fragments have an average length from about 100 and 1000 nucleotides in length.

In some embodiments, the target polynucleotide comprises a linear concatemer having at least one copy of a cell-free polynucleotide sequence, or a complement thereof (e.g., cell-free DNA). A concatemer can have at least one copy of a target sequence from a template polynucleotide (e.g. about or more than about 1, 2, 3, 4, 5, 6, 7, 8, 9, 10, or more copies of the target sequence; in some embodiments, about or more than about 2 copies) linked in tandem. Additional nucleic acid sequences can be interspersed, regularly or irregularly, between the copies of the target sequence.

In some embodiments, a target polynucleotide comprises a sequence variant. A target polynucleotide can comprise a sequence variant such as a single nucleotide polymorphism (SNP), single nucleotide variant, deletion/insertion polymorphism (DIP), a duplication, an inversion, a translocation, a copy number variant (CNV), short tandem repeat (STR), simple sequence repeat (SSR), variable number of tandem repeat (VNTR), amplified fragment length polymorphism (AFLP), retrotransposon-based insertion polymorphism, sequence specific amplified polymorphism, a gene fusion (also referred to as a fusion gene), and differences in epigenetic marks that can be detected as sequence variants (e.g. methylation differences).

In some embodiments, methylation patterns of polynucleotides are analyzed. For analysis of methylation patterns, the ligation product can be treated with bisulfite prior to circularization, and in some cases, after removal of the bridging probe (e.g., via degradation or selective removal). Treatment of a ligation product with bisulfite (e.g., bisulfite treatment) can result in the deamination of unmethylated cytosine to produce uracil in DNA. Methylated cytosines are protected from this conversion to uracil. In subsequent amplification steps, the uracils are amplified as thymines, whereas methylated cytosine residues get amplified as cytosines. Sequencing and subsequent sequence analysis (e.g., detecting C to T mutations) can be used to determine the locations of unmethylated cytosines and methylated cytosines at single-nucleotide resolution.

Some embodiments of the present disclosure comprise primer extension and amplification reactions, such as in generating amplification product. Primer extension reactions can involve changes in temperature (thermocycling) or a constant temperature (isothermal). In some embodiments, primer extension reactions comprise polymerase chain reaction (PCR). PCR typically involves cycling through multiple stages of denaturation, annealing of primer pairs to opposite strands, and primer extension to exponentially increase copy numbers of the target sequence, at least some of these stages generally occurring at different reaction temperatures. Non-limiting examples of PCR amplification techniques are quantitative PCR (qPCR or realtime PCR), reverse transcription PCR (RT-PCR), digital PCR (dPCR or dePCR), target-specific PCR, and quantitative reverse transcription PCR (qRT-PCR). Examples of polymerase enzymes that can be used for PCR are thermostable polymerases, including but not limited to, *Thermus thermophilus* HB8; mutant *Thermus oshimai; Thermus scotoductus; Thermus thermophilus* 1B21; *Thermus thermophilus* GK24; *Thermus aquaticus* polymerase (AmpliTaq® FS or Taq (G46D; F667Y), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerase enzymes that can be used for PCR are non-thermostable polymerases, including, but are not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase.

In some embodiments, a hot start polymerase is used. A hot start polymerase is a modified form of a DNA Polymerase that requires thermal activation. Such a polymerase can be used, for example, to further increase sensitivity, specificity, and yield; and/or to further improve low copy target amplification. Typically, the hot start enzyme is provided in an inactive state. Upon thermal activation the modification or modifier is released, generating active enzyme. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MIDSCI; Minerva Biolabs GmbH; New England Biolabs; Novagen; Promega; QIAGEN; Roche Applied Science; Sigma-Aldrich; Stratagene; Takara Mirus Bio; USB Corp.; Yorkshire Bioscience Ltd; and the like.

In some embodiments, primer extension and amplification reactions comprise isothermal reactions. Non-limiting examples of isothermal amplification technologies are ligase chain reaction (LCR) (e.g. U.S. Pat. Nos. 5,494,810 and 5,830,711); transcription mediated amplification (TMA) (e.g. U.S. Pat. Nos. 5,399,491, 5,888,779, 5,705,365, 5,710,029); nucleic acid sequence-based amplification (NASBA) (e.g. Malek et al., U.S. Pat. No. 5,130,238); signal mediated amplification of RNA technology (SMART) (e.g. Wharam et al., Nucleic Acids Res. 2001, 29, e54); strand displacement amplification (SDA) (e.g. U.S. Pat. No. 5,455,166); thermophilic SDA (Spargo et al., Mol Cell Probes 1996, 10:247-256; European Pat. No. 0684315); rolling circle amplification (RCA) (e.g. Lizardi, "Rolling Circle Replication Reporter Systems," U.S. Pat. No. 5,854,033); loop-mediated isothermal amplification of DNA (LAMP) (e.g. Notomi et al., "Process for Synthesizing Nucleic Acid," U.S. Pat. No. 6,410,278); heliembodiment-dependent amplification (HDA) (e.g. U.S. Pat. Appl. US 20040058378); single primer isothermal amplification (SPIA) (e.g. WO2001020035 and U.S. Pat. No. 6,251,639); and circular helicase-dependent amplification (cHDA) (e.g. U.S. patent application U.S. Ser. No. 10/594,095).

In some embodiments of any of the various aspects of the disclosure, a primer may comprise one or more portions or segments. For example, a primer may comprise one or more amplification primer annealing sequences or complements thereof, one or more sequencing primer annealing sequences or complements thereof; one or more barcode sequences; one or more common sequences shared among multiple different primers; one or more restriction enzyme recognition sites; one or more probe binding sites or sequencing adaptors (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

In some embodiments, a primer comprises a sequencing adaptor element, which generally refers to oligonucleotides incorporated at the 5' and/or 3' ends of polynucleotides to facilitate one or more steps of a polynucleotide sequencing reaction. In some embodiments, a sequencing adaptor is used to bind a polynucleotide comprising the sequencing adaptor to a flow cell for next generation sequencing. Non-limiting examples of next-generation sequencing methods are single-molecule real-time sequencing, ion semiconductor sequencing, pyrosequencing, sequencing by synthesis, sequencing by ligation, and chain termination. Sequencing adaptors for flow cell attachment may comprise any suitable sequence compatible with next generation sequencing systems, e.g., 454 Sequencing, Ion Torrent Proton or PGM, and Illumina X10. Non-limiting examples of sequencing adaptors for next generation sequencing methods include P5 and P7 adaptors suitable for use with Illumina sequencing systems; TruSeq Universal Adapter; and TruSeq Indexed Adapter. In some embodiments, a sequencing adaptor can be used to enrich, e.g., via amplification, such as polymerase chain reaction (PCR), for polynucleotides comprising the adaptor sequence. Sequencing adaptors can further comprise a barcode sequence and/or a sample index sequence.

In some embodiments of any of the various aspects of the disclosure, a ligase is utilized in the formation of a ligation product. Non-limiting examples of enzymes that can be used for ligation reactions are ATP-dependent double-stranded polynucleotide ligases, NAD+ dependent DNA or RNA ligases, and single-strand polynucleotide ligases. Non-limiting examples of ligases are *Escherichia coli* DNA ligase, *Thermus filiformis* DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre®Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants. Ligation reactions can contain a buffer component, small molecule ligation enhancers, and other reaction components.

In one aspect, the present disclosure provides systems for designing bridging probes, first single-stranded adaptors, and/or second single-stranded adaptors for use in forming ligation products. The bridging probes, first single-stranded adaptors, and/or second single-stranded adaptors may comprise any of the features described herein, in relation to any of the various aspects of the disclosure. In some embodiments, the system comprises (a) a computer configured to receive a customer request to design bridging probes, first single-stranded adaptors, and/or second single-stranded adaptors; (b) computer readable medium comprising codes that, upon execution by one or more processors, design at least one bridging probe, at least one first single-stranded adaptors, and/or at least one second single-stranded adaptor; and (c) a report generator that sends a report to a recipient, wherein the report contains sequences of the at least one bridging probe, at least one first single-stranded adaptor, and/or at least one second single-stranded adaptor.

In some embodiments, the computer comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to design bridging probes, first single-stranded adaptors, and/or second single-stranded adaptors for forming a ligation product comprising a single-stranded sample polynucleotide, the sequence of which may be provided by the customer. The computer may receive the customer request directly (e.g. by way of an input device such as a keyboard, mouse, or touch screen operated by the customer or a user entering a customer request) or indirectly (e.g. through a wired or wireless connection, including over the internet).

In some embodiments, the system comprises a report generator that sends a report to a recipient, wherein the report contains sequences of the at least one bridging probe, at least one first single-stranded adaptor, and/or at least one second single-stranded adaptor. The report generator may send a report automatically in response to the customer request. Alternatively, the report generator may send a report in response to instructions from an operator. The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be but is not limited to the customer, or electronic system (e.g. one or more computers, and/or one or more servers). In some embodiments, the report generator sends the report to a recipient's device, such as a personal computer, phone, tablet, or other device. The report may be viewed online, saved on the recipient's device, or printed.

In one aspect, the disclosure provides a computer-readable medium comprising codes that, upon execution by one or more processors, implement a method according to any of the methods disclosed herein. Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Method for Forming a Ligation Product

Ligation of a pair of adapters to a single stranded target DNA molecule is conducted using a biological sample that has a single stranded target DNA molecule in a mixture of single stranded DNA molecules. The single stranded target DNA molecule has a target sequence with extension sequences on the 5' end and the 3' end (FIG. 1, top panel). The ligation reaction is set up using a bridging probe which targets each of the 5' and 3' ends of the single stranded target DNA molecule. The 5' bridging probe base-pairs with the 5' end of the single stranded target DNA molecule and the 3' end of the first adapter and the 3' bridging probe base-pairs with the 3' end of the single stranded target DNA molecule and the 5' end of the second adapter (FIG. 1, bottom panel). Once the complex of single stranded target DNA molecule, bridging probes, and adapters is assembled, ligase is added to the mixture and incubated in order to form a covalent bond between the single stranded target DNA molecule and each adapter. The bridging probes are then removed from the reaction mixture and the target DNA molecule is further amplified and sequenced using the first and second adapter sequences.

Example 2: Method for Forming a Ligation Produce with Imperfect Base-Paring

Ligation of a pair of adapters to a single stranded target DNA molecule is conducted using a biological sample that has a single stranded target DNA molecule in a mixture of single stranded DNA molecules. The single stranded target DNA molecule has a target sequence with extension sequences on the 5' end and the 3' end (FIG. 1, top panel). The ligation reaction is set up using a bridging probe which imperfectly targets each of the 5' and 3' ends of the single stranded target DNA molecule. The 5' bridging probe imperfectly base-pairs with the 5' end of the single stranded target DNA molecule and the 3' end of the first adapter and the 3' bridging probe imperfectly base-pairs with the 3' end of the single stranded target DNA molecule and the 5' end of the second adapter. In some cases, the 5' bridging probe imperfectly base-pairs with the 5' end of the single stranded target DNA molecule forming a single stranded loop in the target DNA molecule (FIG. 2A) or a single stranded loop in the 5' bridging probe (FIG. 2B). In some cases, the 3' bridging probe imperfectly base-pairs with the 3' end of the single stranded target DNA molecule forming a single stranded loop in the target DNA molecule (FIG. 3A) or a single stranded loop in the 3' bridging probe (FIG. 3B). In some cases, the 5' bridging probe imperfectly base-pairs with the 5' end of the single stranded target DNA molecule and the 3' bridging probe imperfectly base-pairs with the 3' end of the single stranded target DNA molecule forming two single stranded loops in the target DNA molecule (FIG. 4A) or a single stranded loop in the 5' bridging probe and a single stranded loop in the 3' bridging probe (FIG. 4B). Once the complex of single stranded target DNA molecule, bridging probes, and adapters is assembled, ligase is added to the mixture and incubated in order to form a covalent bond between the single stranded target DNA molecule and each adapter. The single stranded loops are removed using a nuclease. The bridging probes are then removed from the reaction mixture and the target DNA molecule is further amplified and sequenced using the first and second adapter sequences.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for forming a ligation product comprising a single-stranded sample polynucleotide, wherein the single-stranded sample polynucleotide comprises a target polynucleotide covalently joined to a first extension sequence at a 5' end of the target polynucleotide and to a second extension sequence at a 3' end of the target polynucleotide, the method comprising:
   (a) mixing the single-stranded sample polynucleotide, a first single-stranded adaptor, a second single-stranded adaptor, a first bridging probe, and a second bridging probe to form a polynucleotide complex, wherein the polynucleotide complex includes (i) a 5' end of the first bridging probe specifically hybridized to a 3' end of the first single-stranded adaptor via sequence complementarity, and a 5' end of the single-stranded sample polynucleotide specifically hybridized to a 3' end of the first bridging probe via sequence complementarity, and (ii) a 5' end of the second bridging probe specifically hybridized to a 3' end of the single-stranded sample polynucleotide via sequence complementarity, and a 5' end of the second single-stranded adaptor specifically hybridized to a 3' end of the second bridging probe via sequence complementarity;
   (b) ligating (i) the 3' end of the first single-stranded adaptor to the 5' end of the single-stranded sample polynucleotide and (ii) the 3' end of the single-stranded sample polynucleotide to the 5' end of the second single-stranded adaptor; and
   (c) degrading or selectively removing the first and second bridging probes, thereby forming the ligation product, wherein the single-stranded sample polynucleotide comprises a cell-free deoxyribonucleic acid (DNA).

2. The method of claim 1, wherein the cell-free DNA comprises a sequence variant.

3. The method of claim 2, wherein the sequence variant comprises at least one of a single nucleotide polymorphism, a single nucleotide variant, an insertion, a deletion, a duplication, an inversion, a translocation, a copy number variation, a gene fusion, and a mutation indicative of methylation.

4. The method of claim 1, wherein the first bridging probe hybridizes to at least a portion of the 5' end of the single-stranded sample polynucleotide.

5. The method of claim 1, wherein the second bridging probe hybridizes to at least a portion of the 3' end of the single-stranded sample polynucleotide.

6. The method of claim 1, wherein the first extension sequence and/or the second extension sequence comprises at least one of an amplification primer binding sequence, a sequencing primer binding sequence, a barcode sequence, and a molecular identifier sequence.

7. The method of claim 1, wherein the first single-stranded adaptor and/or the second single-stranded adaptor comprises at least one of an amplification primer binding sequence, a sequencing primer binding sequence, a barcode sequence, and a molecular identifier sequence.

8. The method of claim 1, wherein the first bridging probe, the second bridging probe, or both the first and second bridging probes comprises modified nucleotides.

9. A method for selectively ligating a first single-stranded adaptor and a second single-stranded adaptor to a single-stranded target sample polynucleotide in a reaction mixture comprising non-target sample polynucleotides, the single-stranded target sample polynucleotide comprising a target polynucleotide covalently joined to a first extension sequence at a 5' end of the target polynucleotide and to a second extension sequence at a 3' end of the target polynucleotide, the method comprising:
   (a) hybridizing a 5' end of a first bridging probe to a 3' end of a first single-stranded adaptor via sequence complementarity and a 3' end of the first bridging probe to a 5' end of a single-stranded target sample polynucleotide via sequence complementarity, wherein the 3' end of the first bridging probe does not specifically hybridize to a 5' end of non-target sample polynucleotides;
   (b) hybridizing a 5' end of a second bridging probe to a 3' end of the single stranded target sample polynucleotide via sequence complementarity and a 3' end of the second bridging probe to a 5' end of a second single stranded adaptor via sequence complementarity, wherein the 5' end of the second bridging probe does not specifically hybridize to a 3' end of non-target sample polynucleotides;
   (c) ligating the first single-stranded adaptor to the 5' end of the single-stranded target sample polynucleotide;
   (d) ligating the second single-stranded adaptor to the 3' end of the single-stranded target sample polynucleotide;
   thereby selectively ligating the first single-stranded adaptor and the second single-stranded adaptor to the single-stranded target sample polynucleotide,
   wherein the single-stranded sample polynucleotide comprises a cell-free deoxyribonucleic acid (DNA).

10. The method of claim 9, wherein the cell-free DNA comprises a sequence variant.

11. The method of claim 10, wherein the sequence variant comprises at least one of a single nucleotide polymorphism, a single nucleotide variant, an insertion, a deletion, a duplication, an inversion, a translocation, a copy number variation, a gene fusion, and a mutation indicative of methylation.

12. The method of claim 9, wherein the first bridging probe hybridizes to at least a portion of the 5' end of the single-stranded target sample polynucleotide or the second bridging probe hybridizes to at least a portion of the 3' end of the single-stranded target sample polynucleotide.

13. The method of claim 9, wherein the first bridging probe, the second bridging probe, or both the first and second bridging probes comprises modified nucleotides.

14. The method of claim 9, further comprising degrading or selectively removing the first bridging probe and the second bridging probe.

15. The method of claim 9, wherein the first extension sequence and/or the second extension sequence comprises at least one of an amplification primer binding sequence, a sequencing primer binding sequence, a barcode sequence, and a molecular identifier sequence.

* * * * *